United States Patent
Iizuka

(10) Patent No.: US 8,674,841 B2
(45) Date of Patent: Mar. 18, 2014

(54) SLEEP SYSTEM

(75) Inventor: Hisashi Iizuka, Susono (JP)

(73) Assignee: Toyota Jidosha Kabushiki Kaisha, Aichi-ken (JP)

( * ) Notice: Subject to any disclaimer, the term of this patent is extended or adjusted under 35 U.S.C. 154(b) by 0 days.

(21) Appl. No.: 13/876,323

(22) PCT Filed: Sep. 27, 2011

(86) PCT No.: PCT/IB2011/002237
§ 371 (c)(1),
(2), (4) Date: Mar. 27, 2013

(87) PCT Pub. No.: WO2012/042338
PCT Pub. Date: Apr. 5, 2012

(65) Prior Publication Data
US 2013/0181841 A1  Jul. 18, 2013

(30) Foreign Application Priority Data
Sep. 27, 2010 (JP) ................................ 2010-215322

(51) Int. Cl.
*G08B 23/00* (2006.01)
(52) U.S. Cl.
USPC ..................... 340/575; 340/573.1; 340/4.12
(58) Field of Classification Search
USPC .............. 340/575, 576, 573.1, 4.12; 600/300, 600/508, 529, 509
See application file for complete search history.

(56) References Cited

U.S. PATENT DOCUMENTS

| | | | | |
|---|---|---|---|---|
| 6,265,978 | B1 * | 7/2001 | Atlas | 340/575 |
| 8,009,051 | B2 * | 8/2011 | Omi | 340/575 |
| 2011/0021866 | A1 * | 1/2011 | Iizuka et al. | 600/26 |
| 2011/0319721 | A1 | 12/2011 | Hamaguchi | |

FOREIGN PATENT DOCUMENTS

| | | |
|---|---|---|
| JP | 07-241342 A | 9/1995 |
| JP | 2002-028242 A | 1/2002 |
| JP | 2003-210587 A | 7/2003 |
| JP | 2007-512086 A | 5/2007 |
| JP | 2008-125802 A | 6/2008 |
| JP | 2008-200486 A | 9/2008 |
| JP | 2009-213707 A | 9/2009 |
| JP | 2009-213711 A | 9/2009 |
| JP | 2010-035860 A | 2/2010 |
| JP | 2010-075312 A | 4/2010 |
| JP | 2010-082377 A | 4/2010 |
| JP | 2010-099410 A | 5/2010 |
| JP | 2010-220649 A | 10/2010 |
| WO | 2005/055802 A2 | 6/2005 |
| WO | 2009/112944 A2 | 9/2009 |
| WO | 2010/101183 A1 | 9/2010 |

OTHER PUBLICATIONS

Luca Gammaitoni et al.: "Stochastic resonance", Review of Modern Physics, vol. 70, No. 1, Jan. 1998.

(Continued)

*Primary Examiner* — Toan N Pham
(74) *Attorney, Agent, or Firm* — Sughrue Mion, PLLC

(57) ABSTRACT

A stimulation execution portion of a sleep system applies a stimulus (S112) determined based on the difference between the present sleep depth of a target person (S111), which has been measured by a stimulation effect calculation portion (S105) and a target sleep depth for the target person.

10 Claims, 41 Drawing Sheets

(56) References Cited

OTHER PUBLICATIONS

Report No. 13.2 of Kobayashi Institute of Physical Research, Jul. 1986.

International Search Report and Written Opinion for corresponding International Patent Application No. PCT/IB2011/002237 mailed Jan. 20, 2012.

* cited by examiner

F I G . 10
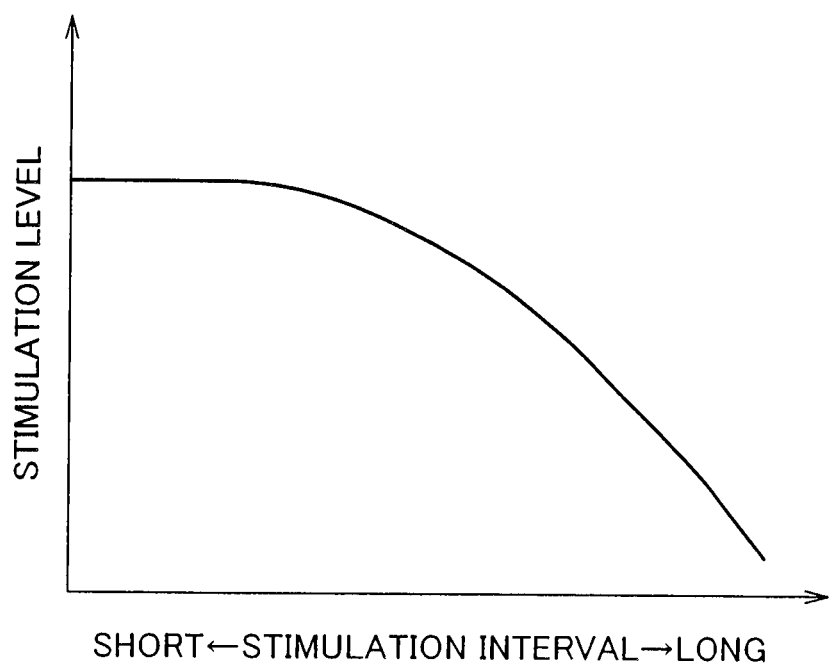

OTHER EXAMPLE

SLEEP SYSTEM

BACKGROUND OF THE INVENTION

1. Field of the Invention

The invention relates to a sleep system, and particularly it relates to a sleep system that stimulates a target person.

2. Description of Related Art

A system has been proposed which is capable of maintaining the sleep depth of a driver, as a user, at a constant level. For example, Japanese Patent Application Publication No. 2009-213711 describes a sleep system that is provided with: a sleep depth determination portion that determines the present sleep depth of the driver; a sleep depth comparison portion that compares, the present sleep depth, determined by the sleep depth determination portion, with a target sleep depth that is a predetermined sleep depth smaller than the maximum sleep depth; and a stimulation control portion and a stimulation device that are used to apply to the user a sensory threshold stimulus of a level based on a human body sensory threshold, when the sleep depth comparison portion determines that the present sleep depth has reached the target sleep depth.

However, for example, when the present sleep depth is very large, the sleep depth may not be properly controlled through a stimulus based on a sensory threshold.

SUMMARY OF THE INVENTION

The invention provides a sleep system that facilitates controlling the sleep depth of a target person to a target sleep depth.

An aspect of the invention relates to a sleep system having a sleep depth measurement portion that measures a present sleep depth of a target person, and a stimulation execution portion that stimulates the target person. The stimulation execution portion is structured to apply a stimulus that is determined based on a difference between the present sleep depth of the target person, which is measured by the sleep depth measurement portion, and a target sleep depth for the target person.

According to the sleep system described above, it is possible to apply, in accordance with the present sleep depth of the target person, a stimulus more appropriate than that applied simply according to the target sleep depth. As such, it is easy to control the sleep depth of the target person to the target sleep depth.

The sleep, system described above may be such that the stimulation execution portion is structured to apply a stimulus of a higher level, the larger the difference between the present sleep depth of the target person and the target sleep depth for the target person.

According to the structure described above, it is possible to apply a stimulus of an appropriate level in accordance with the difference between the present sleep depth of the target person and the target sleep depth for the target person.

The sleep system described above may be such that the stimulation execution portion is structured to apply a stimulus of a higher level, the larger the present sleep depth of the target person.

According to the structure described above, it is possible to apply, a stimulus of an appropriate level in accordance with the present sleep depth of the target person.

The sleep system described above may be such that the stimulation execution portion is structured to stimulate again the target person, regardless of the difference between the present sleep depth of the target person and the target sleep depth for the target person, upon lapse of a predetermined period of time in a case where the sleep depth measurement portion is unable to measure the present sleep depth of the target person after the stimulation execution portion stimulates the target person.

According to the structure described above, even in a case where the present sleep depth of the target person is immeasurable, the target person can be reliably stimulated. As such, for example, it is possible to cope with even a case where a physiological waveform becomes unsteady due to an external disturbance by the stimulation and thus the sleep depth of the target person becomes immeasurable.

The sleep system described above may be such that the sleep depth measurement portion is structured to measure the present sleep depth of the target person based on brainwaves of the target person that develop immediately after the stimulation execution portion stimulates the target person.

According to the structure described above, even in a case where a physiological waveform becomes unsteady due to an external disturbance by the stimulation, the present sleep depth of the target person can be accurately measured by extracting the effect of the stimulation.

The sleep system described above may be such that the stimulation execution portion is structured to apply a stimulus of a higher level, when an amount by which the present sleep depth of the target person changes in response to a stimulus applied by the stimulation execution portion has decreased, or when a frequency at which to apply a stimulus determined based on the difference between the present sleep depth of the target person and the target sleep depth for the target person has decreased.

A decrease in the amount by which the sleep depth of the target person changes in response to the stimulation and a decrease in the frequency at which to apply the stimulus determined based on the difference between the present sleep depth of the target person and the target sleep depth for the target person both indicate that the target person has been adapted to the stimulation and thus the stimulation effect has diminished. According to the structure described above, in such a case, a stimulus of a higher level is applied, and thus it is easy to constantly apply an appropriate stimulus to the target person.

The sleep system described above may be such that the stimulation execution portion is structured to stimulate the target person using at least one of a vibration and a noise around the target person.

According to the structure described above, for example, in a case where the sleep system is incorporated in an automobile, even a small element can provide a high stimulation effect on the target person using vibrations or noises in the automobile.

The sleep system described above may further have a biological reaction amount measurement portion that measures an amount of a biological reaction to a stimulus applied by the stimulation execution portion before the target person falls asleep, wherein the stimulation execution portion is structured to correct a stimulus to be applied to the target person when the target person is asleep, based on the biological reaction amount measured by the biological reaction amount measurement portion before the target person falls asleep.

According to the structure described above, it is easy to properly stimulate each target person regardless of his or her specific individuality and condition.

The sleep system described above may be such that the stimulation execution portion is structured to capable of stimulating multiple positions of the target person and makes a stimulation position correction for stimulation to be performed when the target person is asleep, by changing stimuli applied simultaneously to the multiple positions of the target person, based on an amount of a biological reaction to a stimulus applied to each of the multiple positions of the target person before the target person falls asleep, which has been measured by the biological reaction amount measurement portion.

According to the structure described above, the stimulation execution portion is capable of stimulating the target person at multiple positions, and corrects the position(s) of the target person to which the stimulation is performed when the target person is asleep, based on the amount of the biological reaction to the stimulus applied to each of the positions before the target person fell asleep, which was measured by the biological reaction amount measurement portion. Thus, it is easy to stimulate appropriate positions of each target person, regardless of how he or she is seated on a seat or lies in a bed. Further, the stimulation execution portion corrects the position(s) of the target person to which the stimulation is performed when the target person is asleep, by changing the stimuli applied, respectively, to multiple positions of the target person. As such, even in a case where an intermediate position between the positions to which stimuli can be applied is the position suitable for stimulation, the intimidate position can be properly stimulated by changing the stimuli to be applied, respectively, to the former positions.

The sleep system described above may be such that the stimulation execution portion is structured to correct a stimulus to be applied to the target person, based on at least one of a pressure on a seat on which the target person is seated and a tilt angle of the seat, or at least one of a pressure on a bed in which the target person lies and a tilt angle of the bed.

According to the structure described above, the target person can be properly stimulated, regardless of how the target person is seated or lies and what build the target person has.

The sleep system described above may be such that the stimulation execution portion is structured to stimulate the target person by applying a vibration to the target person, and corrects a stimulus to be applied to the target person based on propagation of the vibration to a body of the target person.

According to this structure, it is easy to stimulate the target person properly, regardless of what build, shape, and body fat ratio the target person has.

Accordingly, the sleep system of the invention facilitates controlling the sleep depth of the target person to the target sleep depth.

BRIEF DESCRIPTION OF THE DRAWINGS

Features, advantages, and technical and industrial significance of exemplary embodiments of the invention-will be described below with reference to the accompanying drawings, in which like numerals-denote like elements, and wherein:

FIG. 10 is a graph illustrating a relation between a stimulation interval and the stimulation level;

DETAILED DESCRIPTION OF EMBODIMENTS

Figure 1:
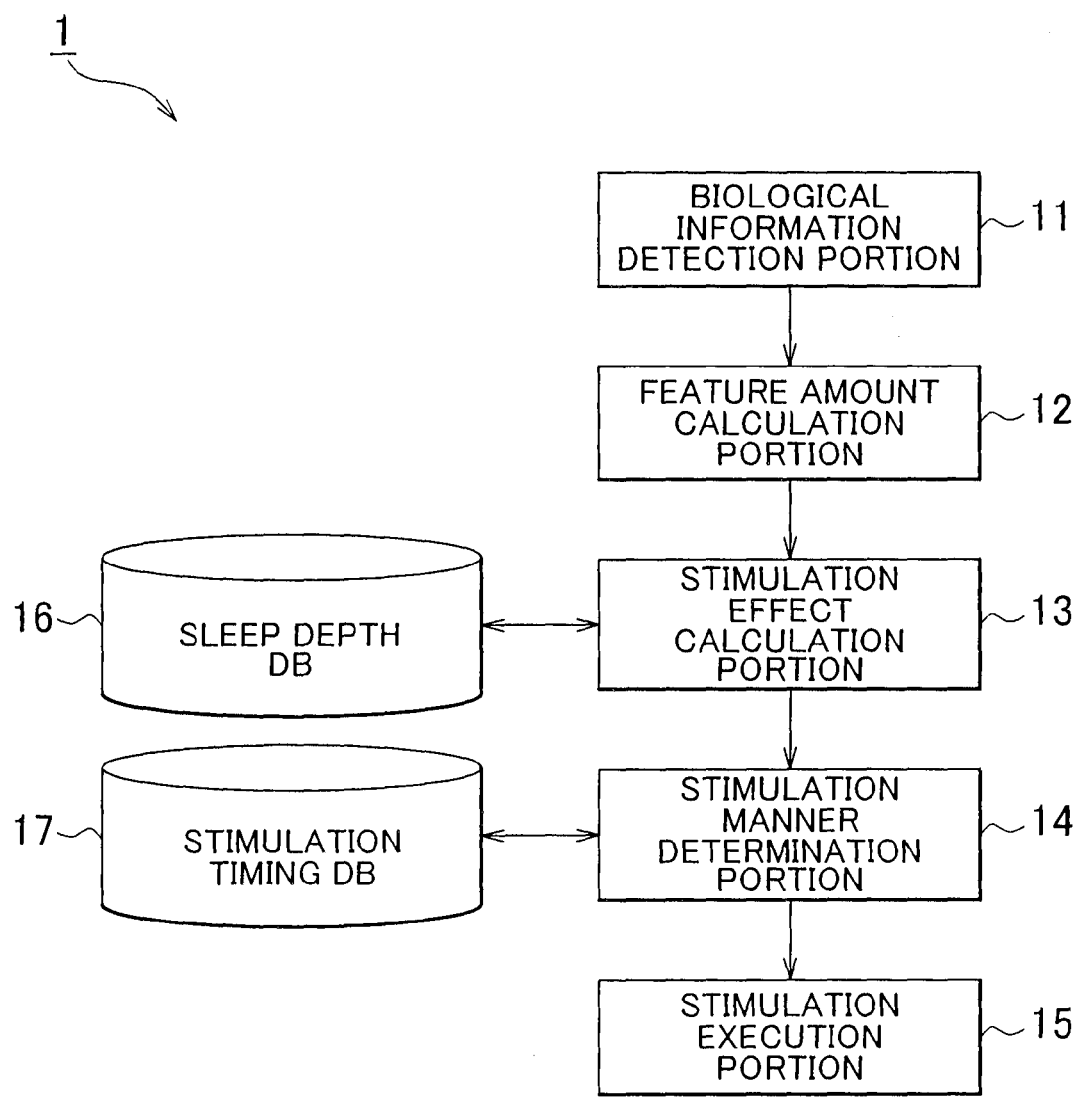
FIG. 1 is a block diagram showing the configuration of a sleep system of an example embodiment of the invention.

Hereinafter, a sleep system according to an example embodiment of the invention will be described with reference to the drawings. The sleep system of the example embodiment is incorporated in a vehicle, or the like, and allows a target person to take a catnap while controlling the sleep depth of the target person to a target sleep depth. Referring to FIG. 1, a sleep system 1 of the example embodiment is provided with a biological information detection portion 11, a feature amount calculation portion 12, a stimulation effect calculation portion 13, a stimulation manner determination portion 14, a stimulation execution portion 15, a sleep depth database 16, and a stimulation timing database 17.

The biological information detection portion 11 obtains information regarding a target person that takes a catnap. The biological information detection portion 11 obtains information necessary for examining the effect of the stimulus applied to the target person (will be referred to as "stimulation effect" where necessary). The information for examining the stimulation effect may be, for example, physiological indicators such as brainwaves, heartbeat, blood pressure, respiration, electrodermal activity, body temperature, and eye movement, and the biological information detection portion 11 may either detect the values of such indicators in a contacting manner or in a non-contacting manner. More specifically, in a case where the sleep system 1 is incorporated in a vehicle, the biological information detection portion 11 may be sensors such as physiological measurement devices and piezoelectric elements provided at a seat and the steering wheel. Further, the biological information detection portion 11 may be adapted to detect specific state amounts of the vehicle, such as a six-degree-of-freedom system vehicle acceleration and speed, using an acceleration sensor(s), a speed sensor(s), or the like.

The feature amount calculation portion 12 calculates feature amounts necessary for examining the stimulation effect, from the biological information obtained from the biological information detection portion 11. The feature amount calculation portion 12 may detect, as the brainwaves stated above, beta waves, alpha waves, theta waves, delta waves, sigma waves, spindle waves, K-complexes, and so on. For brainwaves, alternatively, the feature amount calculation portion 12 may calculate power spectrums in given frequency bands. In a case where a change in the sleep depth is extracted, the feature amount calculation portion 12 may detect the electrodermal activity from wakefulness to light sleep, and the feature amount calculation portion 12 may determine a change in light sleep by detecting a slow eye movement or by detecting a shift of the respiration mode, such as a shift from abdominal respiration to costal respiration.

The stimulation effect calculation portion 13 calculates the stimulation effect or the present sleep depth from the feature amounts obtained from the feature amount calculation portion 12. The stimulation effect calculation portion 13 may examine the sleep depth by applying the obtained brainwaves to a given international criterion standard. Further, the stimulation effect calculation portion 13 may determine the sleep depth from the heartbeat, blood pressure, respiration, electrodermal activity, body temperature, eye movement, and so on. When extracting a change in the sleep depth, the stimulation effect calculation portion 13 may determine the sleep depth according to the electrodermal activity. When determining the sleep depth according to a slow eye movement, the stimulation effect calculation portion 13 may refer to whether the slow eye movement has decreased or whether it has stopped. When extracting the stimulation effect, the stimulation effect calculation portion 13 may refer to the content ratio per unit time, power, average amplitude, or the like, of a given feature waveform(s). The stimulation effect or sleep depth calculated by the stimulation effect calculation portion 13 is recorded in the sleep depth database 16. It is to be noted that the stimulation effect calculation portion 13 serves as "sleep depth measurement portion".

The stimulation manner determination, portion 14 determines the manner in which to stimulate the target person; in accordance with the stimulation effect calculated by the stimulation effect calculation portion 13. The stimulation manner determination portion 14 may determine the stimulation manner in accordance with a condition(s) provided as a map prestored in the stimulation timing database 17. The stimulation manner determination portion 14 may determine the stimulation manner in accordance with a condition(s) defined as a function using the sleep depth as a dependent variable. The stimulation manner determination portion 14 determines the stimulation manner using at least one of the feature amounts used by the stimulation effect calculation portion 13.

Figure 2:
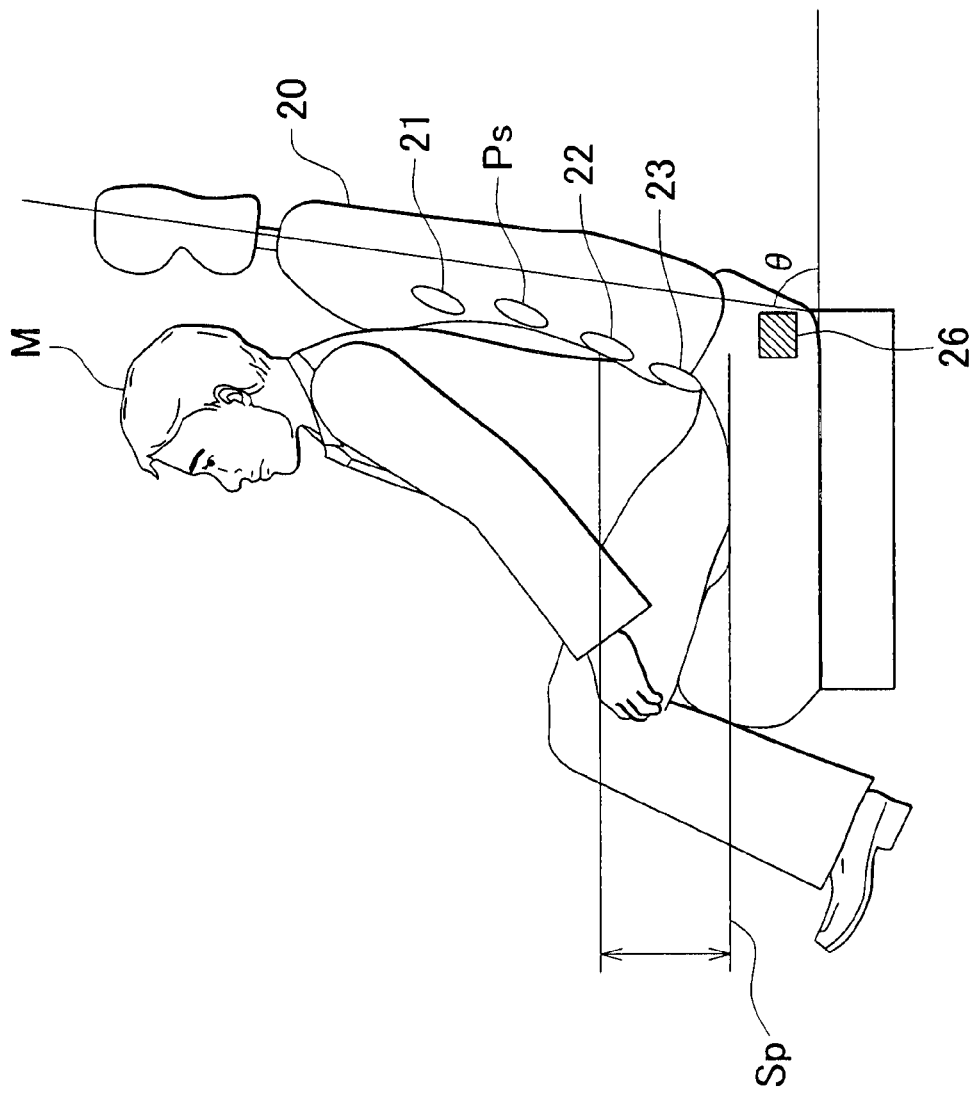
FIG. 2 is a side view of a seat in which devices of the sleep system of the example embodiment are provided.
Figure 3:
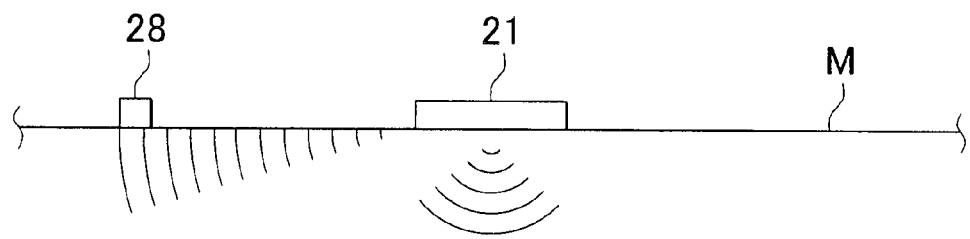
FIG. 3 is a side view showing a vibrator, used for stimulating a target person, and a pressure-acceleration sensor of the sleep system of the example embodiment.

The stimulation execution portion 15 applies a stimulus for maintaining light sleep. The stimulus applied by the stimulation execution portion 15 may be a perceivable stimulus, such as a light, sound (noise), vibration, warmth (or heat), cool air, smell, etc. Referring to FIG. 2, a seat 20 on which a target person M is seated has vibrators 21 to 23. Further, the seat 20 has a seat angle sensor 26 for measuring a tilt angle θ of the seatback. Referring to FIG. 3, the vibrators 21 to 23 each have a pressure-acceleration sensor 28 for measuring the vibration propagating to the body of the target person M. Further, the stimulation execution portion 15 may be adapted to open or close a sunshade, turn an indirect illuminator on, warm the seat 20 up using a seat heater, and/or play music. It is to be noted that the stimulation execution portion 15 serves as "stimulation execution portion".

Figure 4:
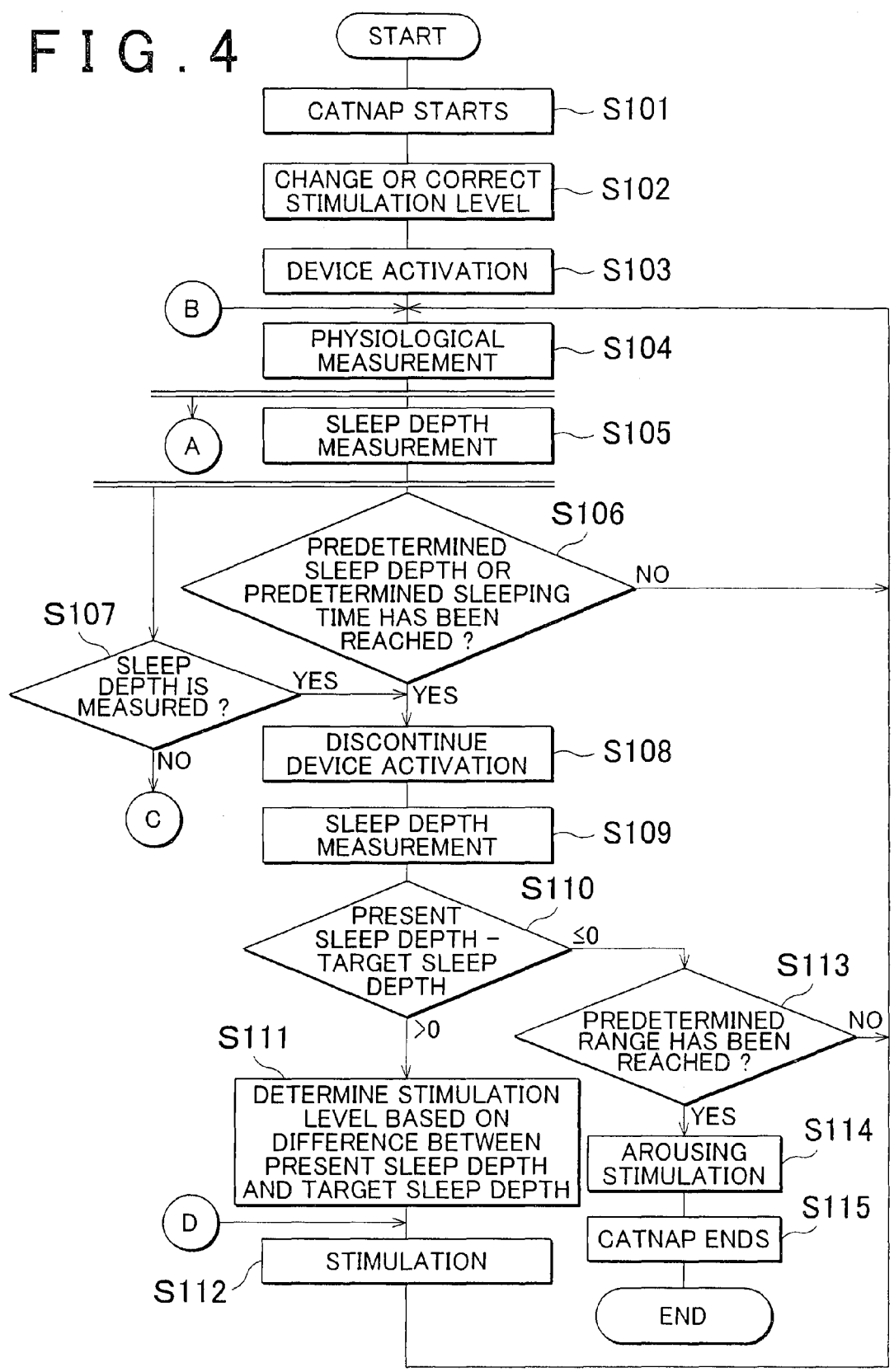
FIG. 4 is a flowchart illustrating a main operation procedure of the sleep system of the example embodiment.

Next, the operation of the sleep system 1 of the example embodiment will be described. Referring to FIG. 4, the target person M pushes a button, or the like, of the sleep system 1 and then starts taking a catnap (S101). The stimulation, effect calculation portion 13 of the sleep system 1 changes and corrects the stimulation level based on various conditions, such as those described later (S102). The stimulation execution portion 15 of the sleep system 1 performs device activation processes, such as opening or closing the sunshade, turning the indirect illuminator on, warming the seat 20 up using the seat heater, and playing music (S103).

The biological information, detection portion 11 of the sleep system 1 detects the values of the physiological indicators including the brainwaves, heart beat, blood pressure, respiration, skin potential, body temperature, and eye movement of the target person M (S104). The biological information detection portion 11 of the sleep system 1 detects information regarding the vehicle state, including the six-degree-of-freedom system vehicle acceleration and speed (S104). The feature amount calculation portion 12 of the sleep system 1 calculates the feature amounts necessary for examining the stimulation effect, from the biological information obtained from the biological information detection portion 11, and the stimulation effect calculation portion 13 of the sleep system 1 measures the present sleep depth of the target person M from the feature amounts obtained from the feature amount calculation portion 12 (S105).

The sleep system 1 executes the processes in S104 and S105 until the sleep depth of the target person M reaches a predetermined sleep depth or until the sleeping time of the target person M reaches a predetermined sleeping time (S106). The processes executed in a case where the stimulation effect calculation portion 13 of the sleep system 1 is unable to measure the sleep depth of the target person M will be described later (S107). When the sleep depth of the target person M reaches the predetermined sleep depth or the sleeping time of the target person M reaches the predetermined sleeping time (S106), the stimulation execution portion 15 of the sleep system 1 discontinues the device activation processes except the opening/closing of the sunshade, that is, it turns the indirect illuminator off, stops the warming of the seat 20 using the seat heater, stops playing music (S108), and so on.

The stimulation effect calculation portion 13 of the sleep system 1 continues to measure the present sleep depth of the target person M (S109). The stimulation manner determination portion 14 of the sleep system 1 calculates the difference between the present sleep depth of the target person M and the target sleep depth (S110). If the present sleep depth is larger than the target sleep depth (S110), the stimulation manner determination portion 14 of the sleep system 1 determines the stimulation level based on the difference between the present sleep depth and the target sleep depth (S111).

Figure 5:
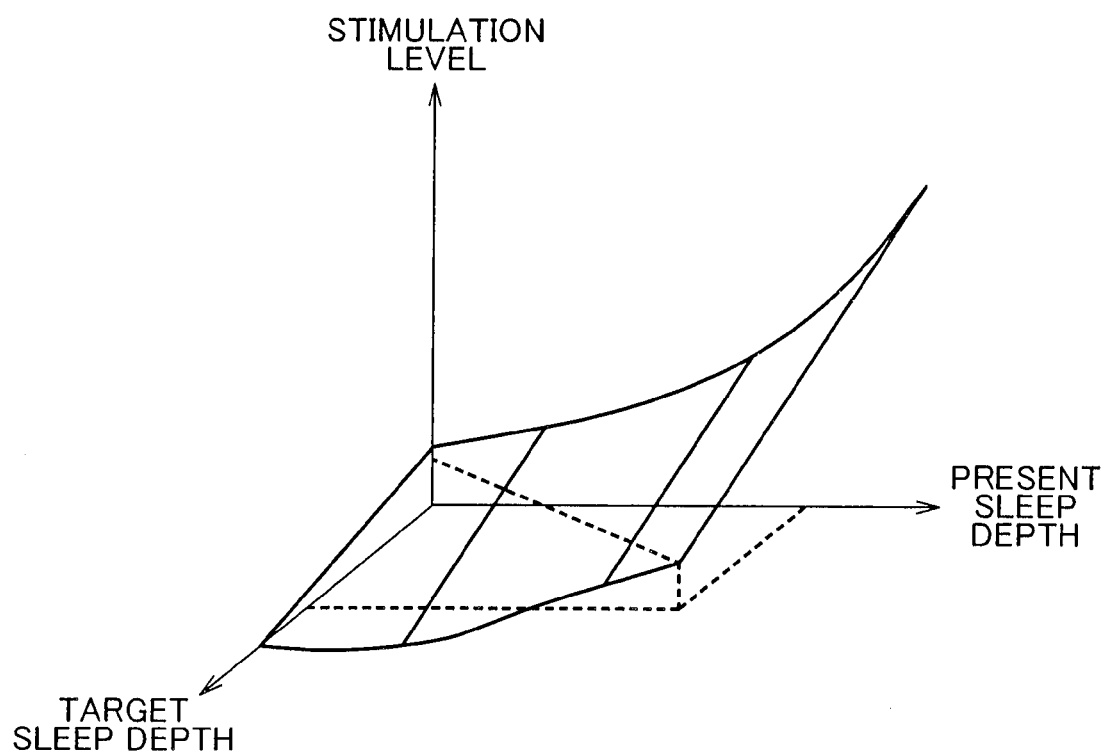
FIG. 5 is a graph illustrating a relation between the present sleep depth, a target sleep depth, and a stimulation level.

A relation between the present sleep depth, the target sleep depth, and the stimulation level, such as the one illustrated in FIG. 5, is stored in the stimulation timing database 17. Referring to the relation shown in FIG. 5, the stimulation manner determination portion 14 of the sleep system 1 calculates the stimulation level based on the present sleep depth and the target sleep depth. Further, the stimulation manner determination portion 14 determines the stimulation manner based on the calculated stimulation level. For example, in a case where vibration is applied as a stimulus through the stimulation execution portion 15, the stimulation manner determination portion 14 determines the duration and amplitude of the vibration.

Figure 6:
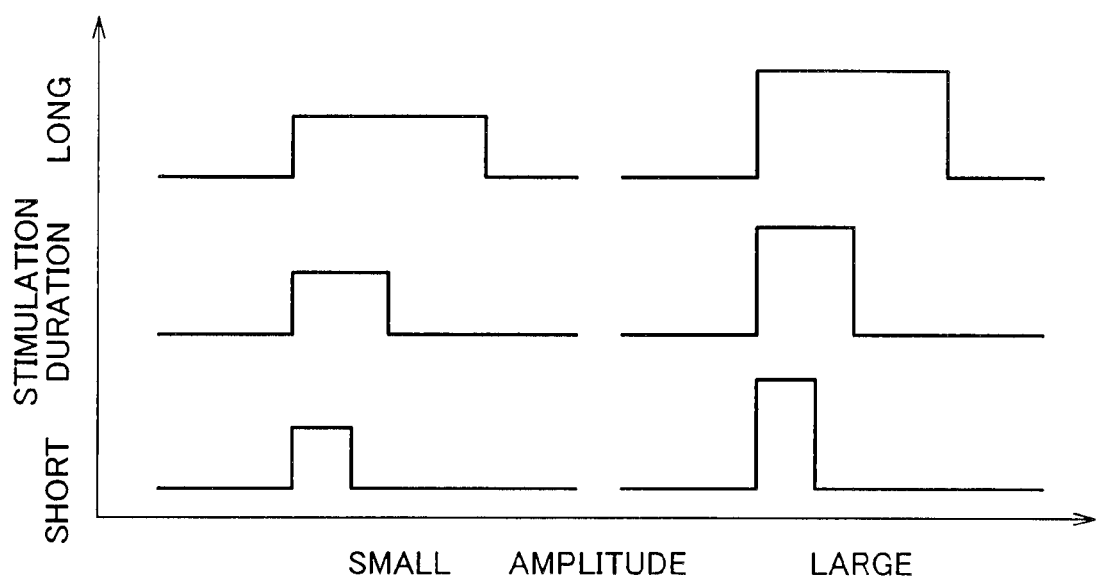
FIG. 6 is a chart illustrating a relation between a stimulation amplitude and a stimulation duration.
Figure 7:
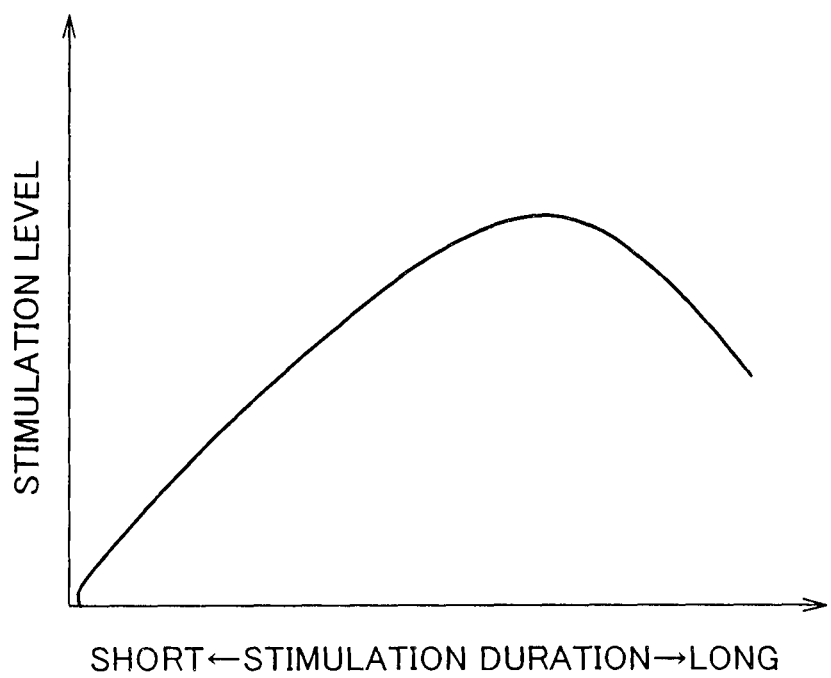
FIG. 7 is a graph illustrating a relation between the stimulation duration and the stimulation level.
Figure 8:
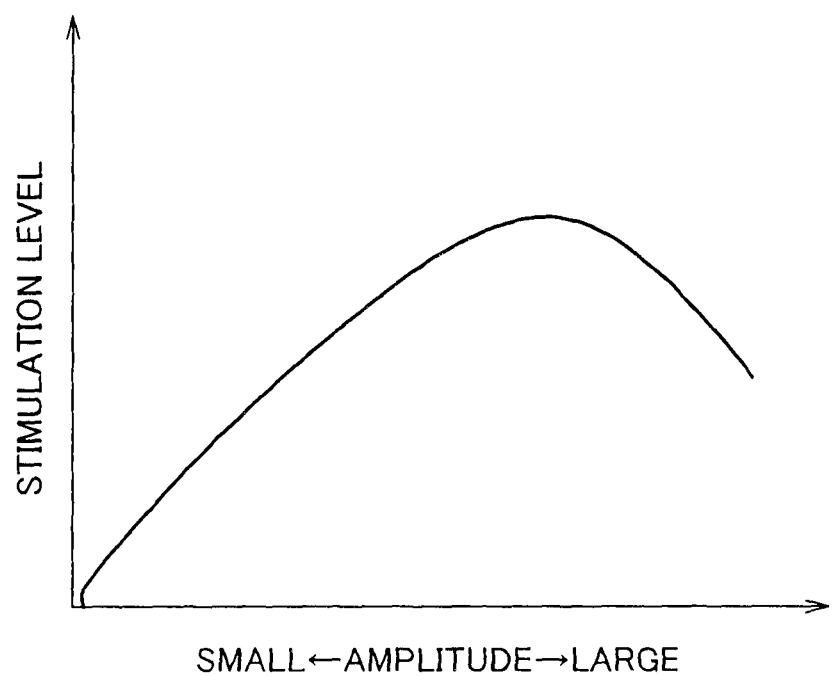
FIG. 8 is a graph illustrating a relation between the stimulation amplitude and the stimulation level.
Figure 9:
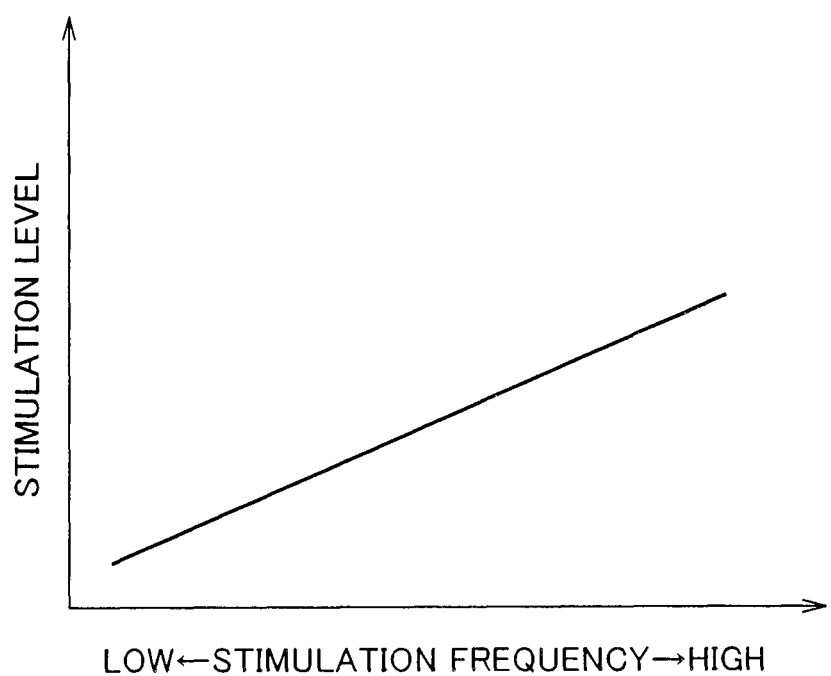
FIG. 9 is a graph illustrating a relation between a stimulation frequency and the stimulation level.

Referring to FIG. 6, normally, the stimulation level is higher, the larger the amplitude of the vibration applied as a stimulus, and the longer its duration. That is, the stimulation level increases from the lower-left side toward the upper-right side of FIG. 6. Further, for cases where vibration is applied as a stimulus, a detailed relation between the stimulation level and the stimulation duration, a detailed relation between the stimulation level and the amplitude, a detailed relation between the stimulation level and the stimulation frequency, and a detailed relation between the stimulation level and the stimulation interval, such as those illustrated in FIGS. 7 to 10, are stored in the stimulation timing database 17. The stimulation maimer determination portion 14 adjusts the stimulation level based on its relations with the respective parameters for adjusting the stimulation level, such as the stimulation duration, amplitude, stimulation frequency, and stimulation interval, which are stored in the stimulation timing database 17. For example, when the target person M is to be aroused, the stimulation manner determination portion 14 sets the stimulation duration longer than when the target person M is to be maintained in light sleep.

Alternatively, the stimulation manner determination portion 14 may determine the stimulation level using a function, such as a multinomial expression, using the values of the parameters for adjusting the stimulation level. Further, alternatively, the stimulation manner determination portion 14 may change the stimulation level, factoring in the stimulation time interval, the time for which the stimulation has been continued, and the present sleep depth.

Figure 11:
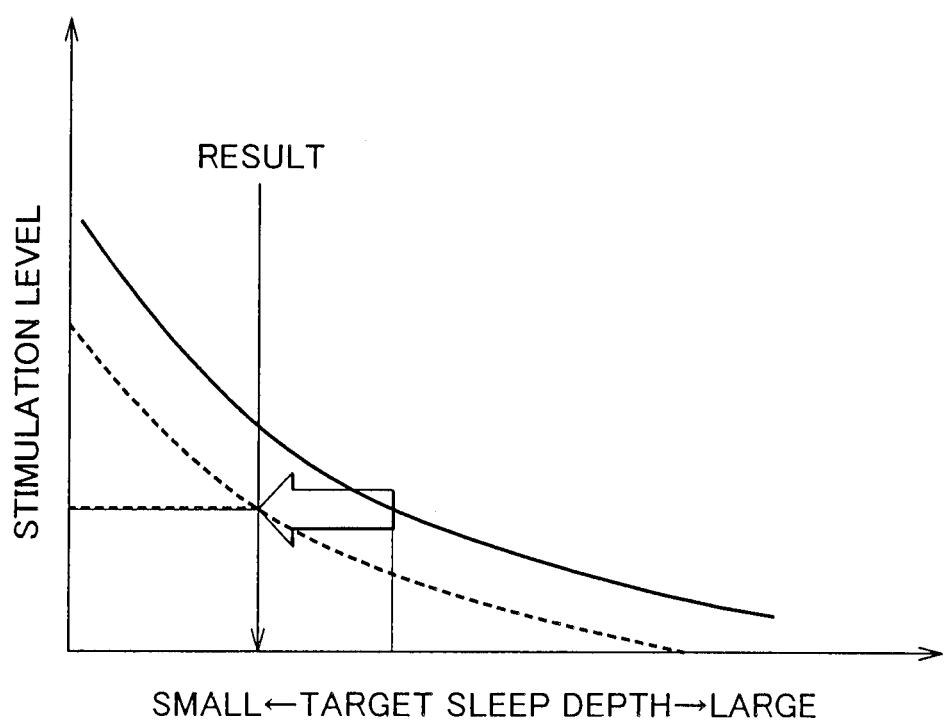
FIG. 11 is a graph illustrating a relation between the target sleep depth and the stimulation level, in which the present sleep depth in FIG. 5 is regarded as being constant.
Figure 12:
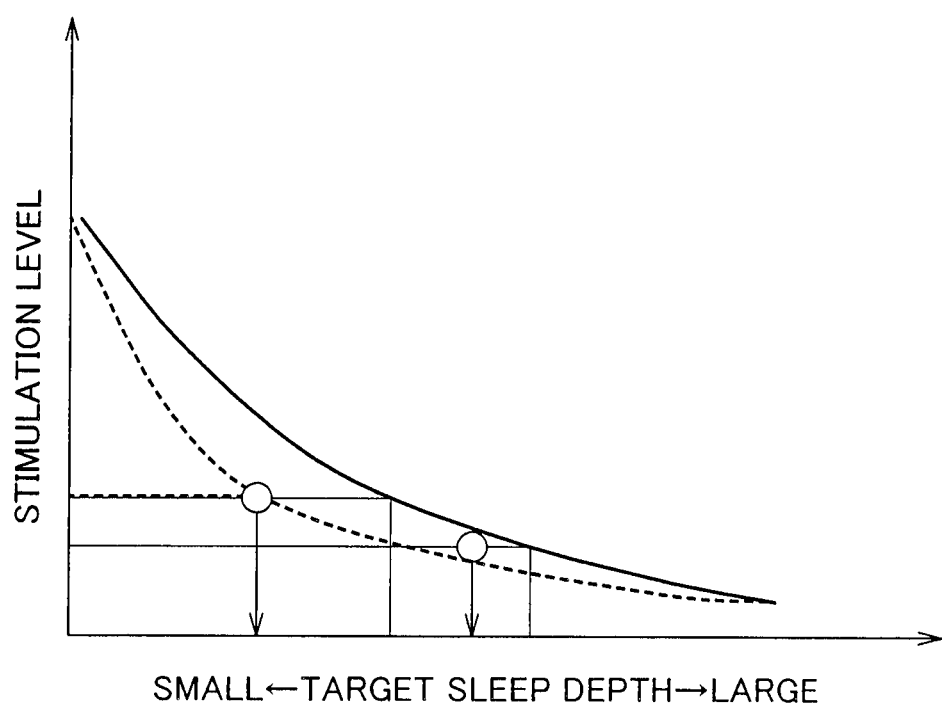
FIG. 12 is a graph illustrating a case where the stimulation illustrated in FIG. 11 is performed to multiple positions and different results are obtained at them.

The stimulation manner determination portion 14 may be adapted to specify and learn the individuality of the target person if the effect of the stimulation is different, due to his or her peculiar sensitivity characteristic, from that extracted from the table prestored in the stimulation timing database 17. Such learning can be accomplished using the following stimulation effect rating method. For example, referring to FIG. 11, in a case where the result indicated by the broken lines in FIG. 5, which is different from the prestored value indicated by the solid lines, is obtained while the present sleep depth is fixed in the map illustrated in FIG. 5, the stimulation manner determination portion 14 may change the values stored in the stimulation timing database 17 for each individual target person based on the values indicated by the broken lines. Further, referring to FIG. 12, in a case where results different from the prestored values indicated by the solid curve are obtained at two or more points, the stimulation manner determination portion 14 may change the values stored in the stimulation timing database 17 for each individual target person based on the results at the same points, as represented by the broken curve in FIG. 12.

Figure 13:
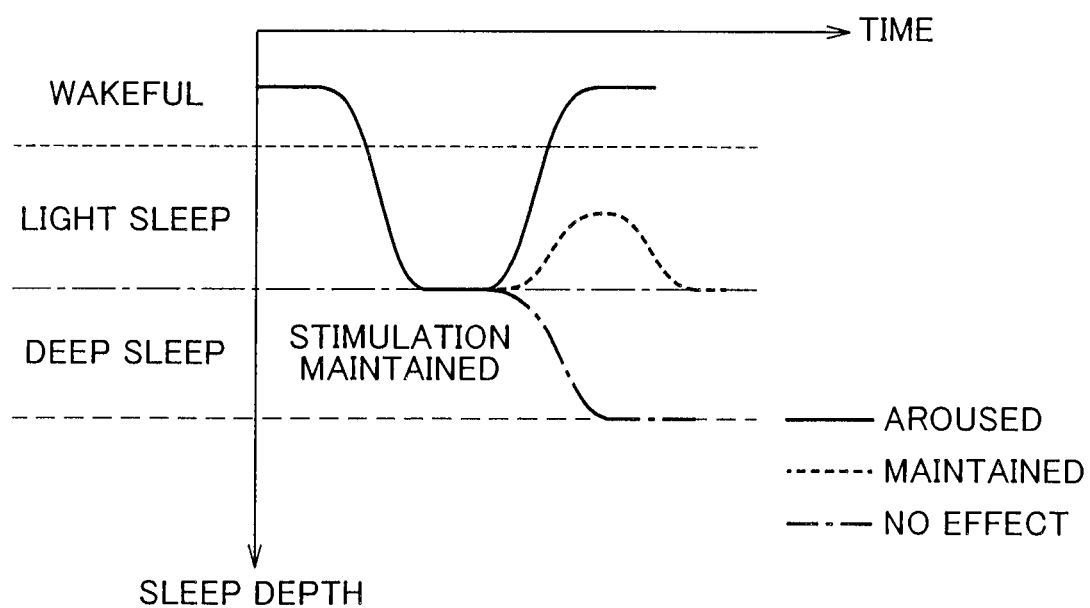
FIG. 13 is a chart illustrating how the sleep depth changes in each of a case where the target person is aroused by the stimulation, a case where the sleep depth of the target person is maintained after the stimulation, and a case where no effect is obtained from the stimulation.
Figure 14:
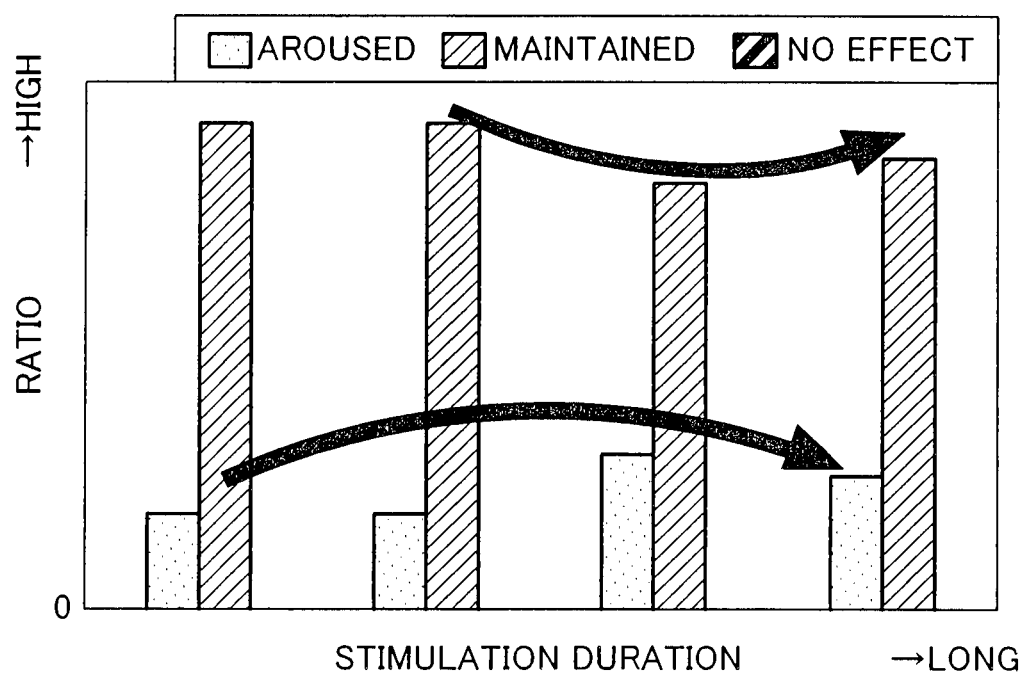
FIG. 14 is a graph showing a relation between the stimulation duration and the ratio of the case where the target person is aroused by the stimulation, a relation between the stimulation duration and the ratio of the case where the sleep depth of the target person is maintained after the stimulation, and a relation between the stimulation duration and the ratio of the case where no effect is obtained from the stimulation.
Figure 15:
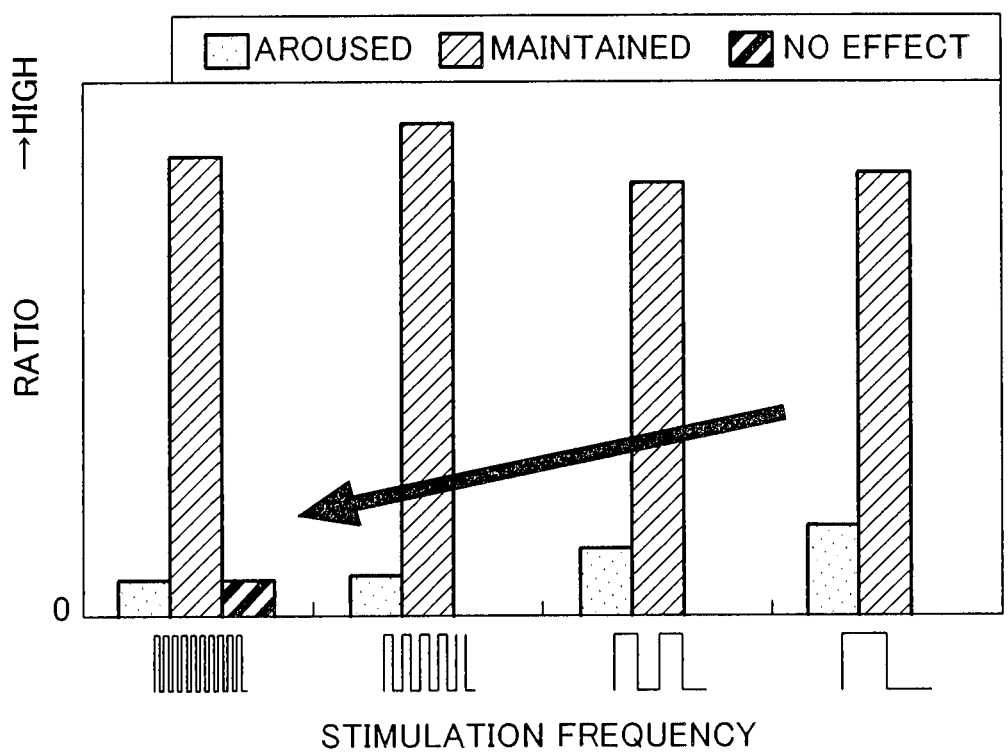
FIG. 15 is a graph showing a relation between the stimulation frequency and the ratio of the case where the target person is aroused by the stimulation, a relation between the stimulation frequency and the ratio of the case where the sleep depth of the target person is maintained after the stimulation, and a relation between the stimulation frequency and the ratio of the case where no effect is obtained from the stimulation.
Figure 16:
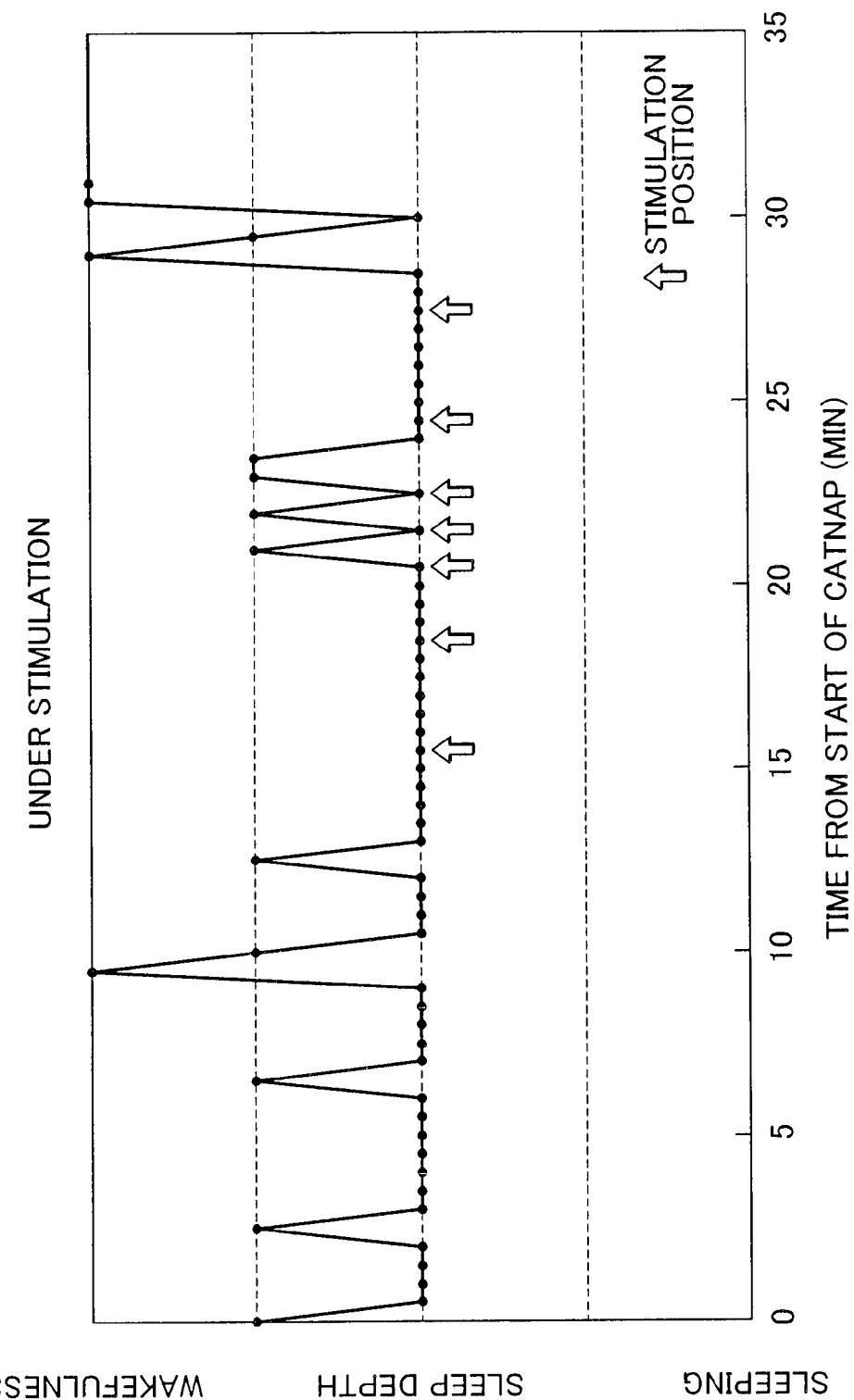
FIG. 16 is a chart illustrating how the sleep depth of a test subject changes from the start of a catnap under stimulation.
Figure 17:
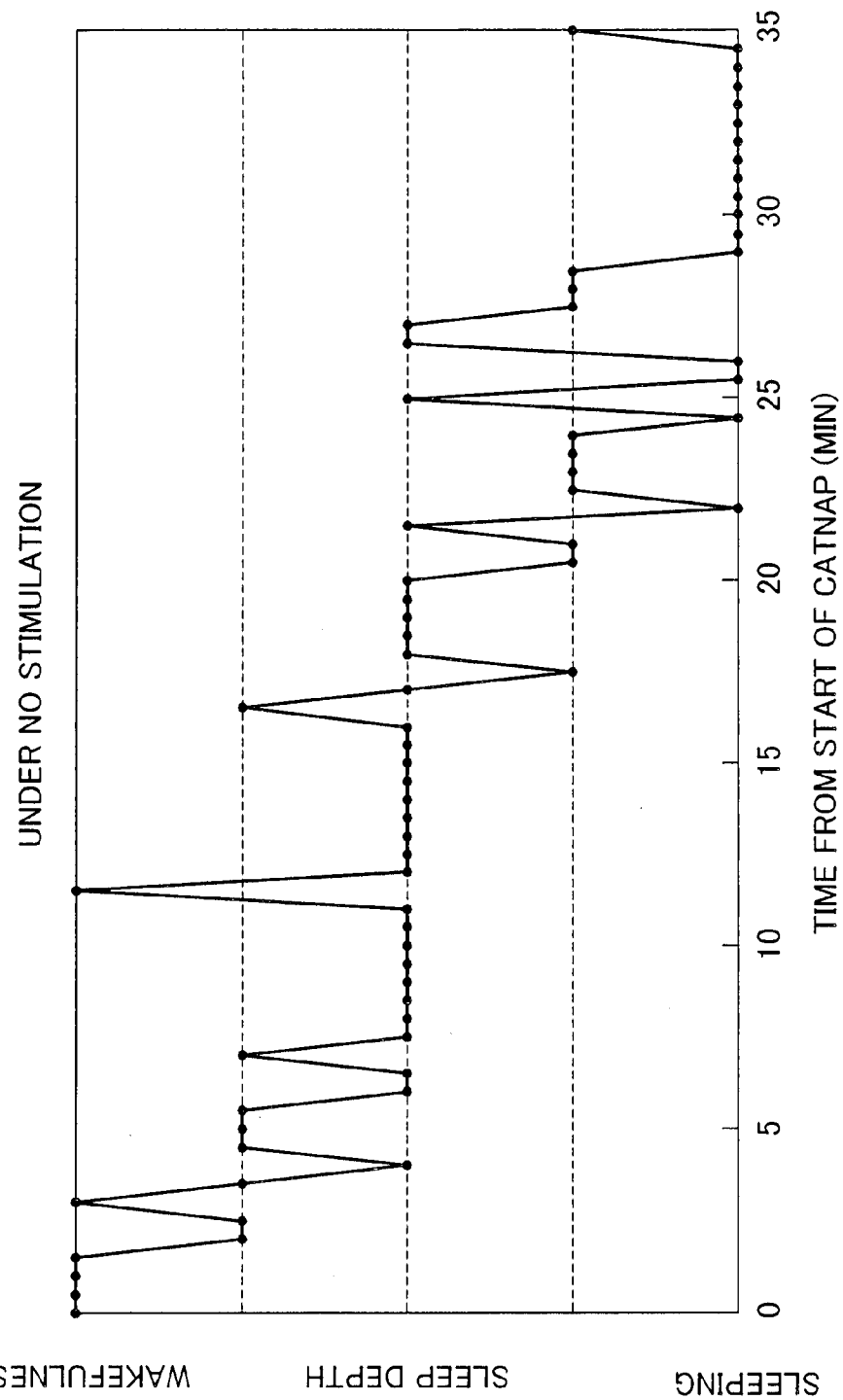
FIG. 17 is a chart illustrating how the sleep depth of the same test subject of FIG. 16 changes from the start of a catnap under no stimulation.

Meanwhile, it is known that, in fact, the responses of sensory organs improve according to the rate and amount of a cutaneous change, and as illustrated in FIG. 13, the consequence of continuing the stimulation can vary between the three: the target person being aroused; the sleep depth being maintained; and no effect being obtained. The graph in FIG. 14 illustrates the ratio, with respect to each stimulation duration, between the case where the target person is aroused, the case where the sleep depth is maintained, and the case where no effect is obtained. The graph in FIG. 15 illustrates the ratio, with respect to each stimulation frequency, between the case where the target person is aroused, the case where the sleep depth is maintained, and the case where no effect is obtained. Further, the chart in FIG. 16 illustrates how the sleep stage shifts while the stimulation on the target person is continued, and the chart in FIG. 17 illustrates how the sleep stage shifts while the same stimulation is not performed. As is understood from these charts, the target person can either be maintained in light sleep or aroused by changing the stimulation manner.

Referring back to FIG. 4, the stimulation execution portion 15 stimulates the target person M using the stimulation manner determined by the stimulation manner determination portion 14 (S112). On the other hand, if the present sleep depth is not larger than the target sleep depth (S110), the sleep system 1 repeats the processes in S104 to S110 until the present sleep depth reaches a predetermined range, that is, the target sleep depth or until the sleeping time reaches a predetermined range; that is, the target sleeping time (S113). When the present sleep depth reaches the target sleep depth or the sleeping time reaches the target sleeping time (S113: YES), the stimulation execution portion 15 applies an arousing stimulus to the target person M (S114). As a result, the target person M wakes up, that is, his or her catnap ends (S115).

Figure 18:
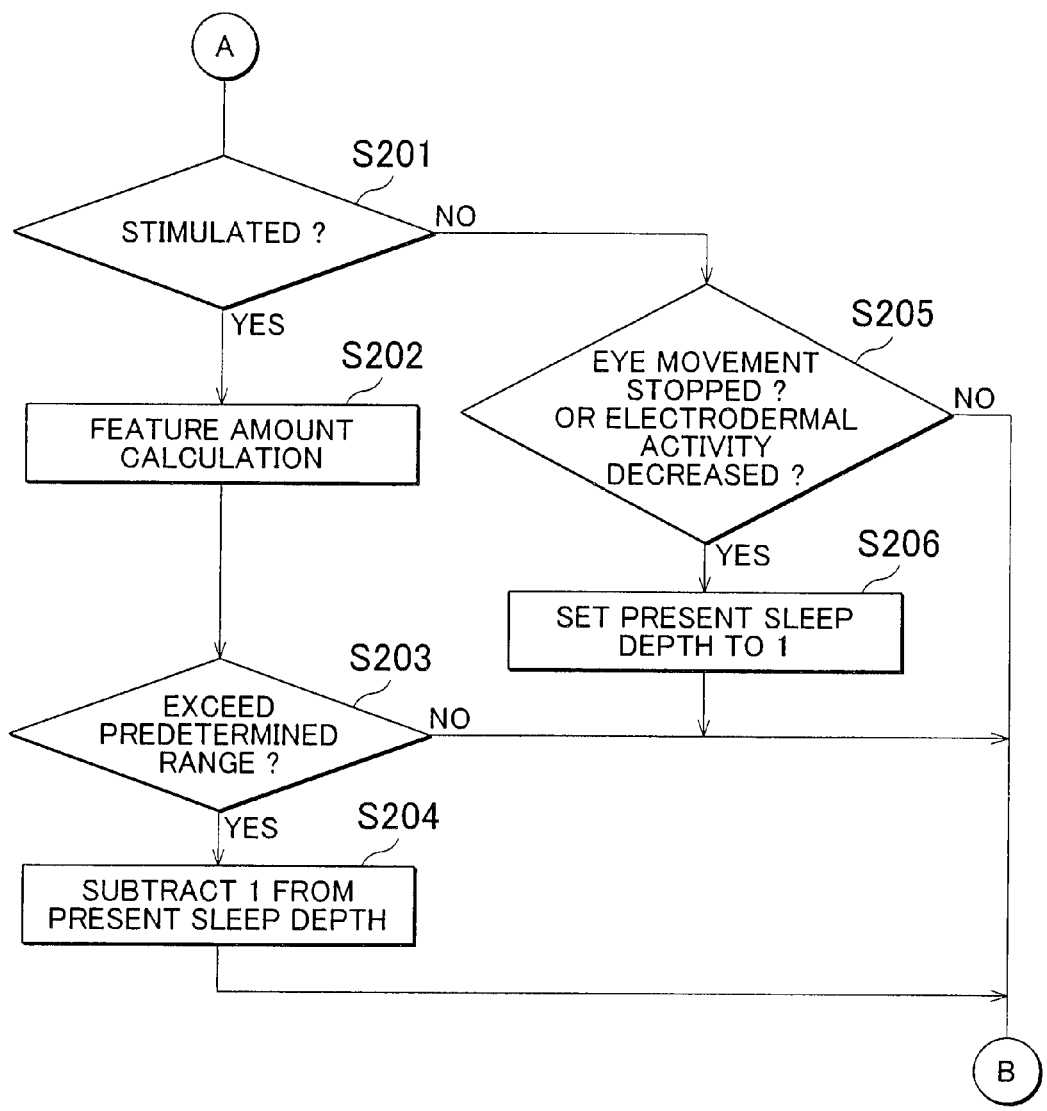
FIG. 18 is a flowchart illustrating an operation procedure for factoring in the effect of the stimulation performed in the operation procedure illustrated in FIG. 4.

Hereinafter, a stimulation effect rating method applicable to the sleep system 1 of the example embodiment will be described. A physiological waveform of the target person M becomes unsteady immediately after the start of stimulation. Thus, the stimulation effect calculation portion 13 of the sleep system 1 measures the sleep depth of the target person M from the form of brainwaves that develop immediately after the start of stimulation, while measuring the sleep depth of the target person M (S105). Referring to FIG. 18, when the stimulation execution portion 15 stimulates the target person M (S201), the feature amount calculation portion 12 of the sleep system 1 calculates feature amounts of brainwaves, such as the amplitude, time percentage, and frequency (S202).

Figure 19:
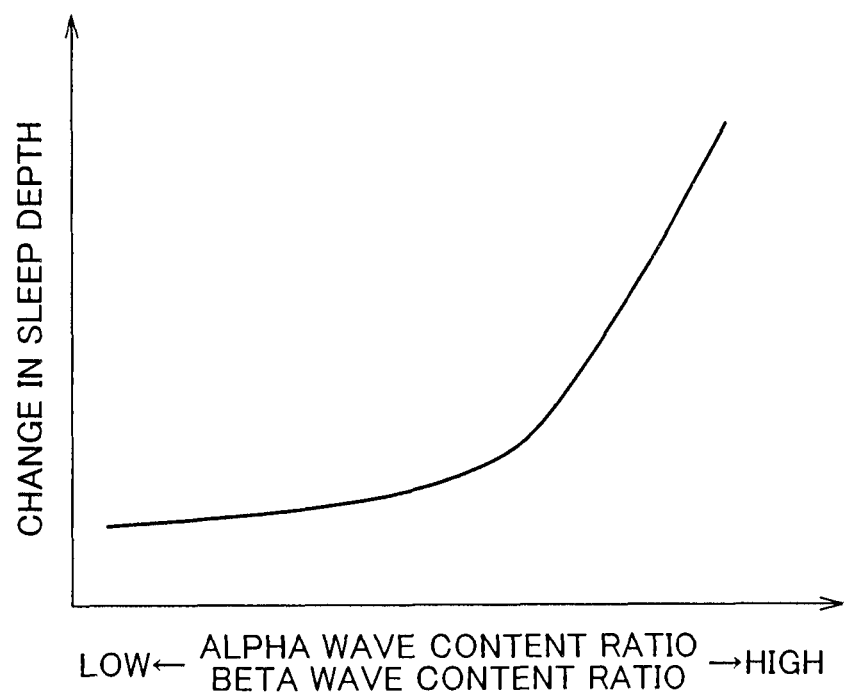
FIG. 19 is a graph illustrating a relation between a change in the sleep depth and the content ratios of alpha and beta waves.
Figure 20:
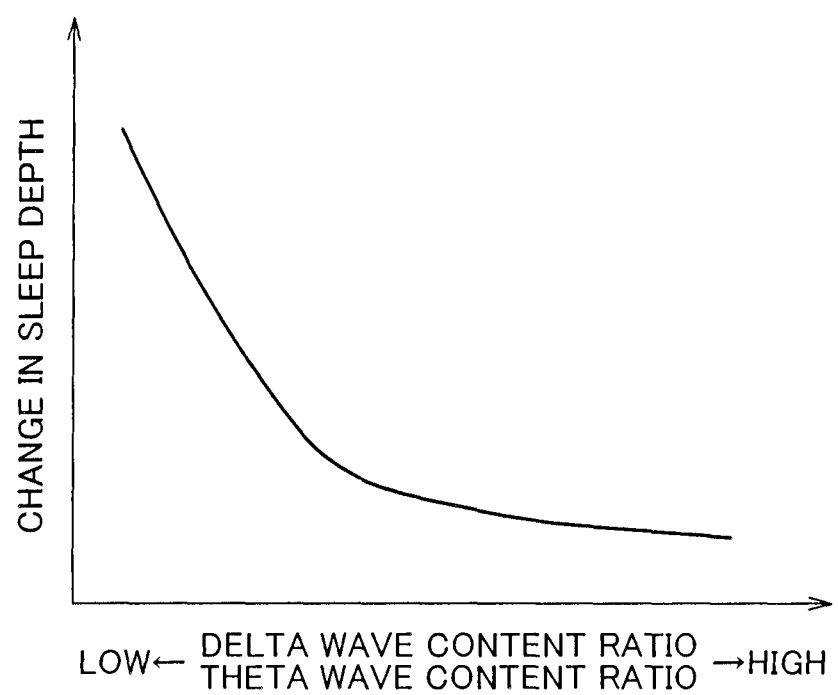
FIG. 20 is a graph illustrating a relation between a change in the sleep depth and the content ratios of delta and theta waves.

Next, how the sleep depth changes and how the brainwave form changes will be described focusing on brainwaves by way of example. The levels of alpha and beta waves tend to be high during wakefulness. Thus, as shown in FIG. 19, alpha and beta waves increase as the sleep depth decreases and then an arousal occurs. On the other hand, the levels of delta and theta waves increase as the sleep depth increases. Thus, as shown in FIG. 20, delta and theta waves decreases as an arousal occurs. The amplitude of K-complexes that occur during stimulation is correlational with the reaction to the stimulation. The level of sigma waves that promote the sleep tends to be higher, the stronger the arousing stimulus. In view of this, the stimulation effect calculation portion 13 measures the sleep depth of the target person M, factoring in these feature amounts.

The stimulation effect calculation portion 13 uses, as a parameter(s) for measuring the sleep depth, at least one of the amplitude of K-complexes and the content ratios or time percentages of beta, alpha, theta, delta, and sigma waves. The stimulation effect calculation portion 13 may measure the sleep depth by determining whether an AND condition is satisfied for at least two waveforms, such as alpha wave/theta wave, alpha wave/beta wave, alpha wave/delta wave, beta wave/theta wave, and beta wave/delta wave. The stimulation effect calculation portion 13 may measure the sleep depth using a function, such as a multinomial expression, using these parameters. When the applied stimulus is significantly weak, the stimulation effect calculation portion 13 may measure the values of the respective parameters multiple times using one or more of the methods described above and determine the sleep depth based on the average of the measured values. Further, the stimulation effect calculation portion 13 may rate the stimulation effect from how or how much the value of each parameter changes in response, to the stimulation being started (e.g., a difference between a value obtained before the start of stimulation and a value obtained after it).

Figure 21:
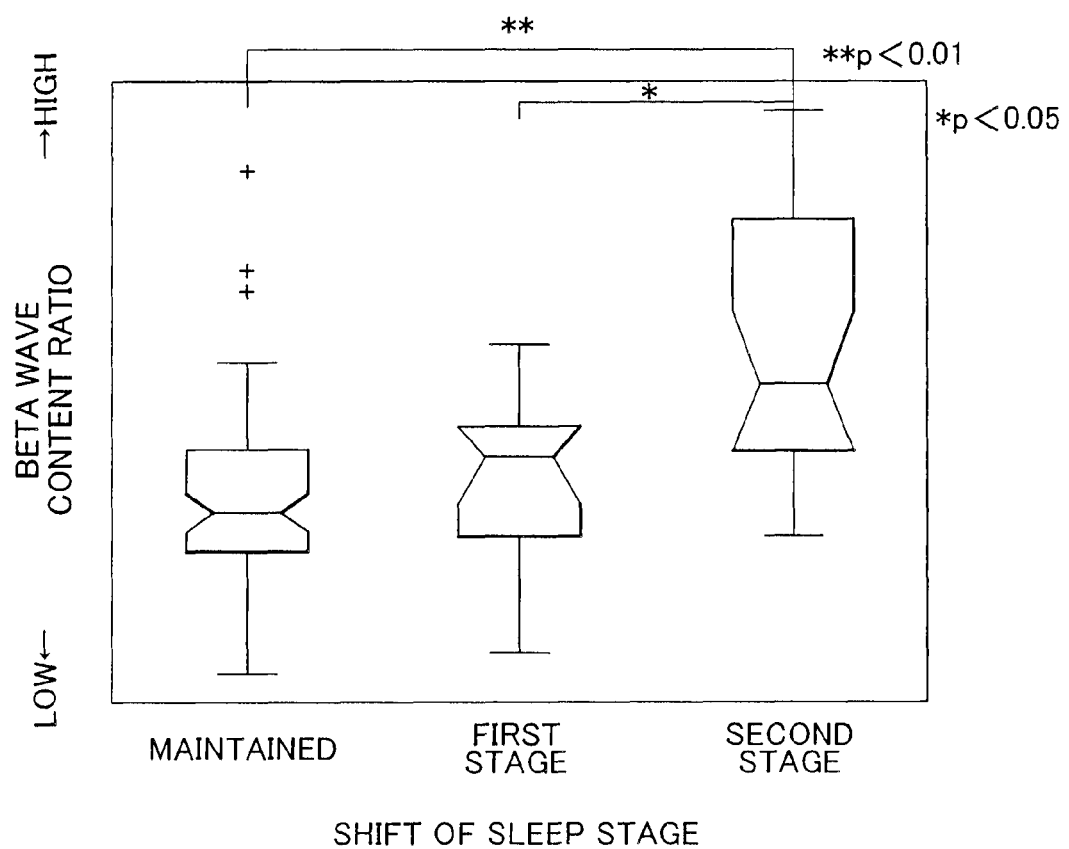
FIG. 21 is a graph illustrating a relation between the shift of the sleep stage and the bate wave content ratio.

For example, it is known that the ratio of a given feature brainwave (e.g., alpha waves) and the amplitude of K-complexes change depending upon the perceptivity or sensitivity to stimulation. However, such changes are normally regarded as noises, and they have never been associated with changes in the sleep depth. In this example embodiment, therefore, the sleep depth and stimulation effect are quantified using such feature waveforms. For example, the chart in FIG. 21 illustrates a relation between the variation of the sleep depth and the content ratio of beta waves as a feature waveform, which is found when stimulation is started from the sleep depth corresponding to the sleep stage 2. Bate waves are a feature waveform that develops during wakefulness with the eyes open. As is known from FIG. 21, there is a significant correlation between the content ratio of beta waves and the degree of wakefulness.

Referring back to FIG. 18, when the feature amount exceeds the predetermined range (S203), the stimulation effect calculation portion 13 subtracts 1 from the present sleep depth (S204). On the other hand, in a case where the stimulation is not performed (S201), if a stoppage of the eye movement or a decrease in the electrodermal activity is detected (S205), the stimulation effect calculation portion 13 sets the present sleep depth to 1 (S206). On the other hand, in a case where the stimulation is not performed (S201), if no stoppage of the eye movement or no decrease in the electrodermal activity is detected (S205), the biological information detection portion 11 executes the process in S104 shown in FIG. 4 again.

Next, the methods that the sleep system 1 of the example embodiment uses to determine the stimulation timing and confirm the stimulation effect when the sleep depth is immeasurable will be described. The inventors have discovered that the time for which the sleep depth is maintained depends on the sleep depth after the start of stimulation, not the sleep depth immediately before it. In view of this, in the example embodiment, the time that elapses after the start of stimulation is measured to confirm the stimulation timing and the stimulation effect.

Figure 22:
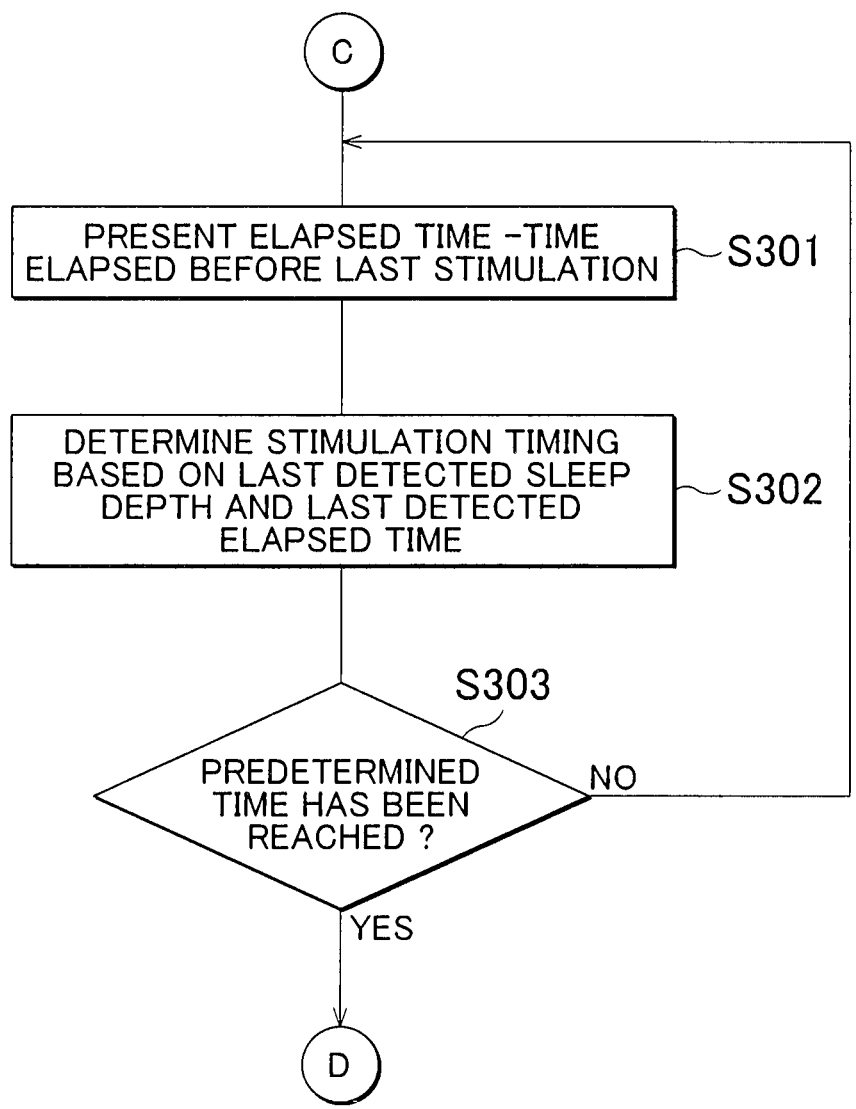
FIG. 22 is a flowchart illustrating an operation procedure that is executed when the sleep depth of the target person has failed to be measured in the operation procedure illustrated in FIG. 4.

When the sleep depth is immeasurable (S107) during the control procedure illustrated in FIG. 4, the stimulation manner determination portion 14 of the sleep system 1, as shown in FIG. 22, subtracts the time elapsed before the last stimulation 1 from the present elapsed time (S301). Then, the stimulation manner determination portion 14 determines the stimulation timing from the sleep depth detected last (i.e., the latest detected sleep depth) and the elapsed time detected last (i.e., the latest detected elapsed time) (S302). When a predetermined time is reached (S303), as shown in FIG. 4, the stimulation execution portion 15 of the sleep system 1 performs the stimulation (S112).

Figure 23:
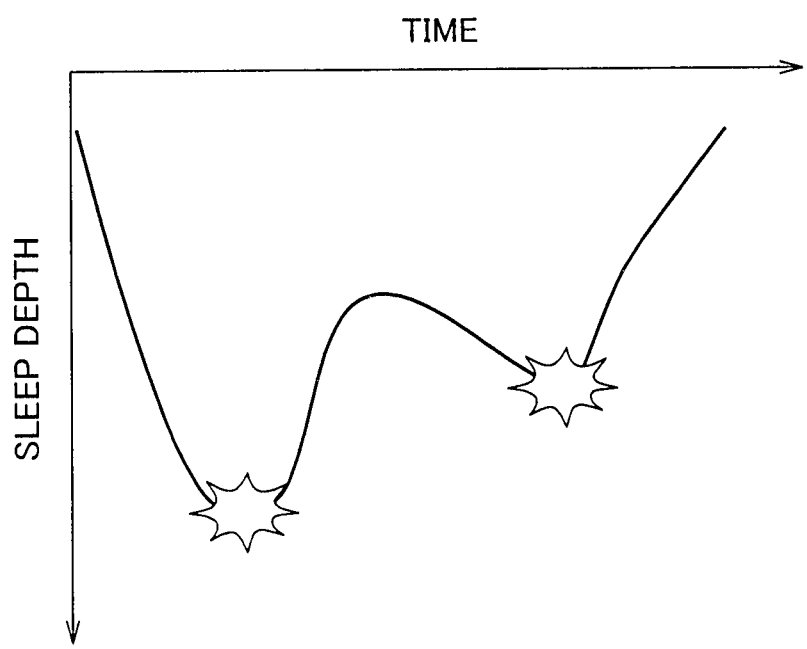
FIG. 23 is a graph between the stimulation timing and the sleep depth.

The stimulation manner determination portion 14 determines the stimulus to be applied. This determination is allowed on the condition that the tendency of variation of the sleep depth that will be caused by the selected stimulus is known. The stimulation manner determination portion 14 applies the stimulus after the sleep depth reaches a given sleep depth. For example, in a case where the target person M is to be maintained in light sleep, the stimulation manner determination portion 14 applies the stimulus at predetermined time intervals. With regard to methods for determining the stimulation timing other than those using brainwaves, it is possible to determine that a shift from light sleep to deep sleep has occurred, when the respiration mode has changed from costal respiration to abdominal respiration, when the respiratory sound has come to include a sleep sound; and when the heart beat has changed. Further, it is possible to determine that a shift from wakefulness to light sleep has occurred, for example, when the slow eye movement has decreased and when the electrodermal activity has decreased. Referring to FIG. 23, in a case where the target person M is to be gradually aroused from light sleep, the time interval of the stimulation can be determined in accordance with the gradient of the sleep depth at the time the target person M fell asleep. This gradient may be either determined using a function or a map.

With regard to the method for confirming the stimulation effect, for example, the stimulation effect may be calculated from the time that elapsed from the last stimulation to the next stimulation. That is, for example, after the stimulus was applied at the boundary between a light sleep state, before the beginning of the catnap, where the sleep depth is small and a deep sleep state where the sleep depth is large, if the time taken for the sleep depth to reach the boundary between the light sleep state and the deep sleep state is equal to or longer than a predetermined time, it indicates that the stimulus provided an arousing effect.

Figure 24:
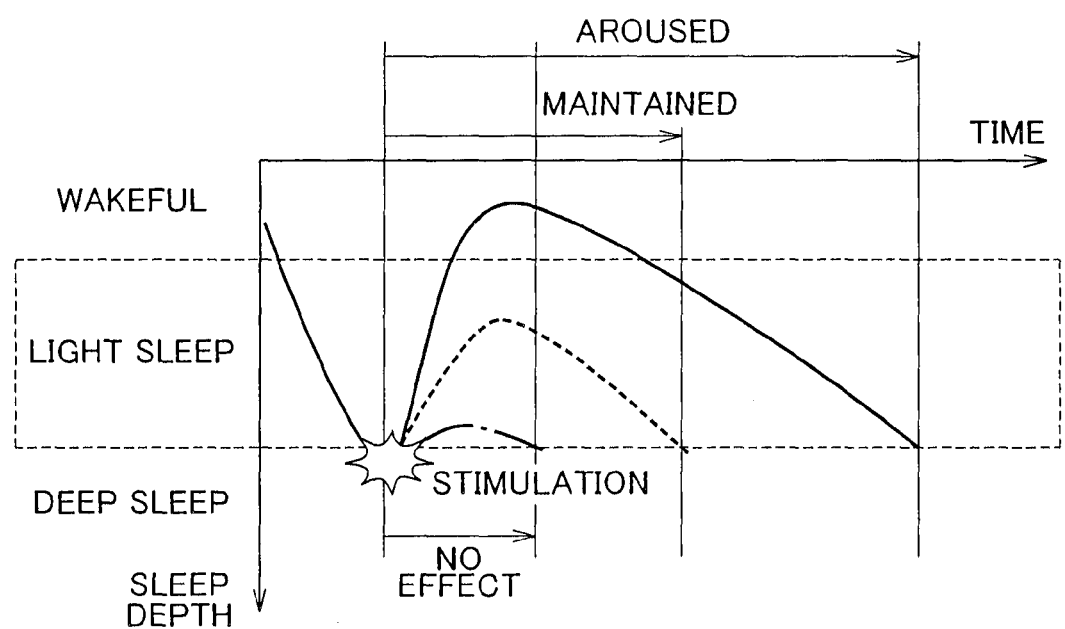
FIG. 24 is a chart illustrating the time taken for the sleep depth of the target person to return to the previous sleep depth after the stimulation in a case where the target person is aroused by the stimulation, the same time taken in a case where the sleep depth of the target person is maintained after the stimulation, and the same time taken in a case where no effect is obtained from the stimulation.
Figure 25:
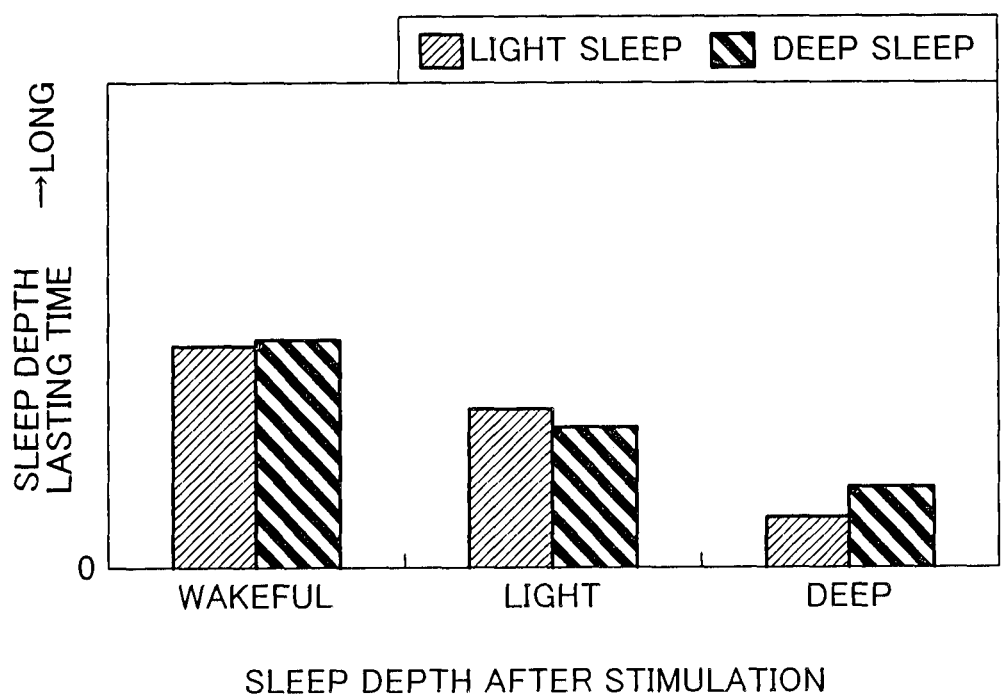
FIG. 25 is a graph illustrating the time for which the sleep depth of the target person remains unchanged in a case where the target person has been aroused after the stimulation performed when the target person was in light sleep, the time for which the sleep depth of the target, person remains unchanged in a case where the target person has been aroused after the stimulation performed when the target person was in deep sleep, the time for which the sleep depth of the target person remains unchanged in a case where the sleep depth of the target person has been maintained after the stimulation performed when the target person was in light sleep, the time for which the sleep depth of the target person remains unchanged in a case where the sleep depth of the target person has been maintained after the stimulation performed when the target person was in deep sleep, the time for which the sleep depth of the target person remains unchanged in a case where no effect has been obtained by the stimulation performed when the target person was in light sleep, and the time for which the sleep depth of the target person remains unchanged in a case where no effect has been obtained by the stimulation performed when the target person was in deep sleep.

For example, the chart in FIG. 24 illustrates a relation of the time that elapses from when the sleep depth changes to a given sleep depth after applying the stimulus to when the sleep depth returns to the previous sleep depth, which is found in a case where the stimulus is applied at the boundary between a light sleep state where the sleep depth is small and a deep sleep state where the sleep depth is large. Further, the chart in FIG. 25 illustrates a relation between the sleep depth after the application of the stimulus and the time the same sleep depth remains unchanged, which is found for each of a case where the sleep depth immediately before the application of the stimulus is small and a case where the same sleep depth is large. As is understood from FIGS. 24 and 25, the time that elapses before the sleep depth reaches the given sleep depth differs depending upon the sleep depth after the application of the stimulus, not the sleep depth immediately before it.

Figure 26:
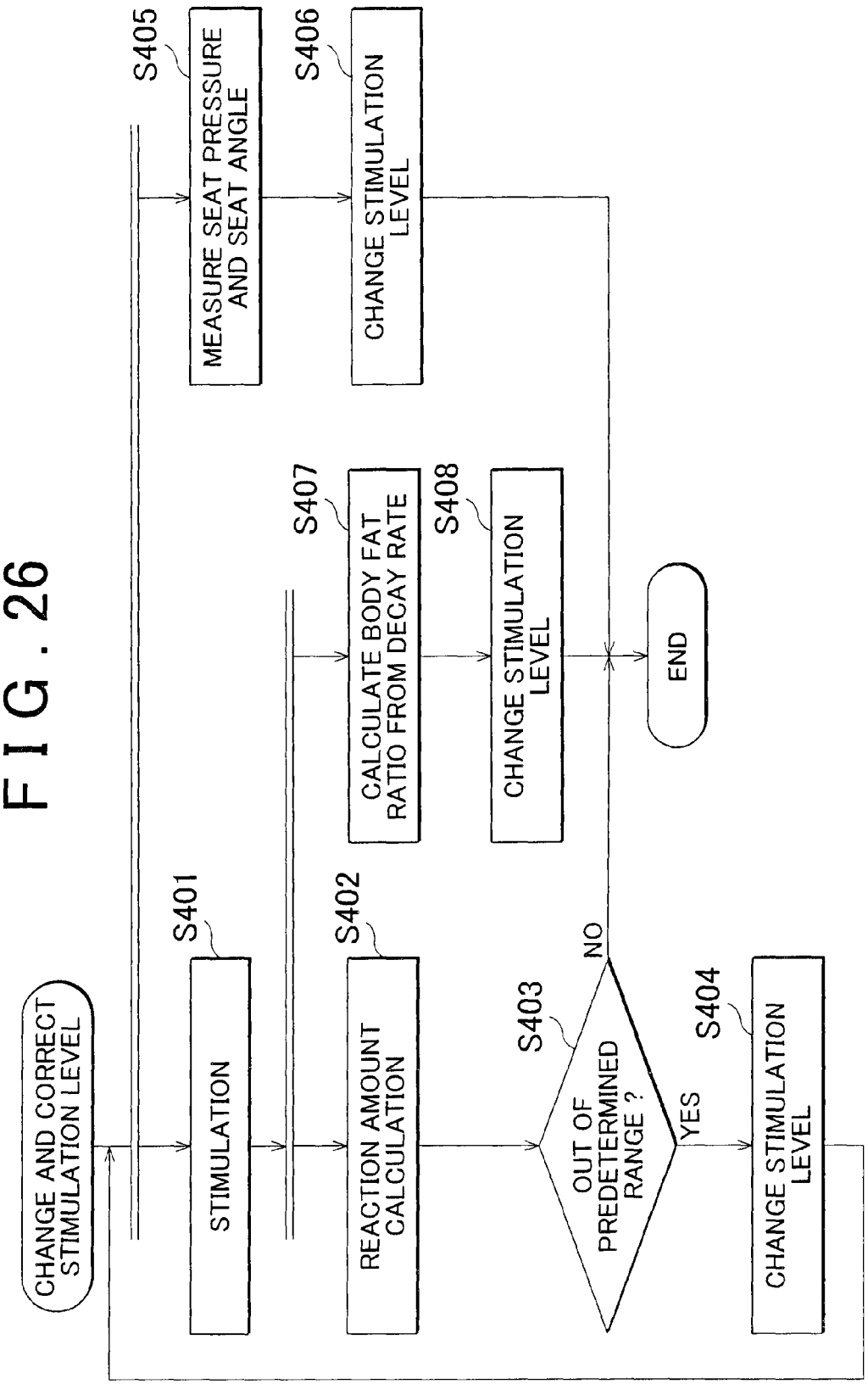
FIG. 26 is a flowchart illustrating an operation procedure for changing and correcting the stimulation level in the operation procedure illustrated in FIG. 4.

Hereinafter, the methods that the sleep system 1 of the example embodiment uses to change and correct the stimulation level will be described in detail. In this example embodiment, the stimulation level and the stimulation manner are determined based on a change in a physiological waveform that occurs immediately after the stimulation. In the following, by way of example, a case where the positions to which to apply the stimulus (will be referred to as "stimulation positions" where necessary) are determined will be described. Referring to FIG. 26, after stimulation (S401), the stimulation manner determination portion 14 of the sleep system 1 calculates a reaction amount from a change of the physiological waveform (S402). This physiological waveform may be, for example, the electrodermal activity (EDA) and/or brainwaves. Alternatively, the reaction amount may be determined using a weighted average of these.

The stimulation manner determination portion 14 then compares the reaction amount with a threshold thereof, and if the reaction amount is out of a threshold range (S403), the stimulation manner, determination portion 14 changes the stimulation manner by changing, for example, the stimulation level or stimulation position (S404). Note that the stimulation manner determination portion 14 may make the comparison described above using a relative change in the reaction amount and the absolute value thereof. The stimulation manner determination portion 14 selects the optimum position from among multiple stimulation positions as a relative change in the reaction amount. Further, the stimulation manner determination portion 14 compares a reaction amount extracted from reaction amount information prestored in the stimulation timing database 17, etc. with the actually measured reaction amount, and if the stimulation effect is weak, the stimulation manner determination portion 14 changes the stimulation manner. When the measured reaction amount data includes only one measurement result, the stimulation manner determination portion 14 may execute a process using a predetermined threshold may be executed. Further, when the measured reaction amount data includes multiple measurement results, for determination, the stimulation manner determination portion 14 may refer to their average or may perform statistical testing on them.

Figure 27:
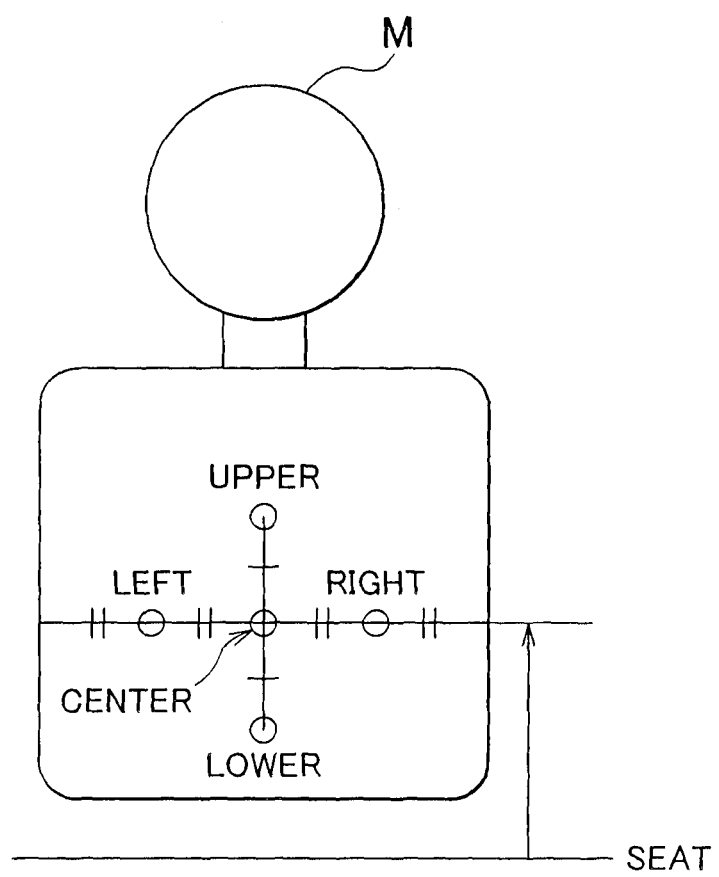
FIG. 27 is a view illustrating the stimulation positions of the target person.
Figure 28:
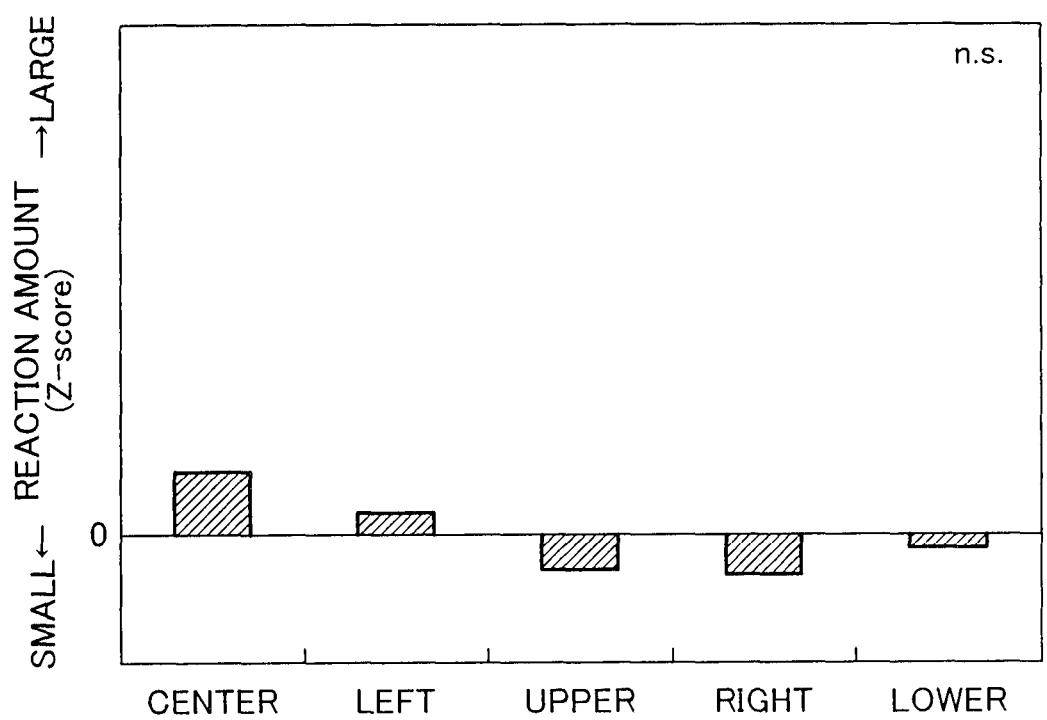
FIG. 28 is a graph illustrating a relation between each of the stimulation positions shown in FIG. 27 and the electrodermal activity.
Figure 29:
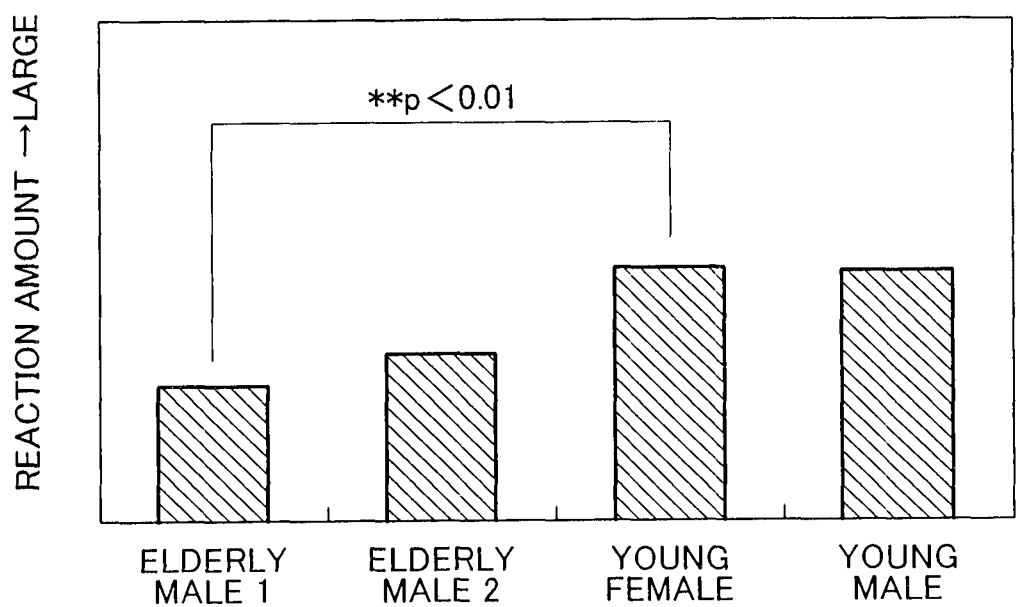
FIG. 29 is a graph illustrating the biological reaction amounts of persons classified by generation and sex.

For example, in a case where various positions of the target person M, such as the low back and the back as shown in FIG. 27 are stimulated, the electrodermal activity reaction amounts shown in the chart in FIG. 28 are measured. As is known from FIG. 28, no significant difference is found between the reaction amounts at the respective stimulation positions. In such a case, therefore, the stimulation manner determination portion 14 determines that any of these positions may be selected as the stimulation position. The chart in FIG. 29 illustrates the ratio of a palm EDA to a lower back EDA, which is found with each of target persons M classified by generation and sex. If these ratios are standardized, their absolute values can be compared. For example, each target person M is made to touch, on his or her palm, the vibrator provided at the armrest of the seat 20, and then standardization is performed using the values of "the value of reaction (EDA) to the vibration on the back/the value of reaction (EDA) to the vibration on the palm".

In such cases, preferably, multiple vibrators (i.e., the vibrators 21 to 23) are provided, respectively, at the position corresponding to the second lumbar of the target person M, a position that is a predetermined distance higher than it, and a position that is a predetermined distance lower than it, as shown in FIG. 2, although a single vibrator may be provided at a position that is in contact with the back, buttocks, or thighs of the target person M. That is, regardless of what build each target person M has, the backbone always bends at the second lumber, and the second lumber always contacts the seat when the target person M is seated on the seal, and further, for example, the distances from a seat SP to the respective positions are constant regardless of the age (18 to 65 years old) and sex of the target person M. Thus, preferably, these positrons are used as standard stimulation positions.

Figure 30:
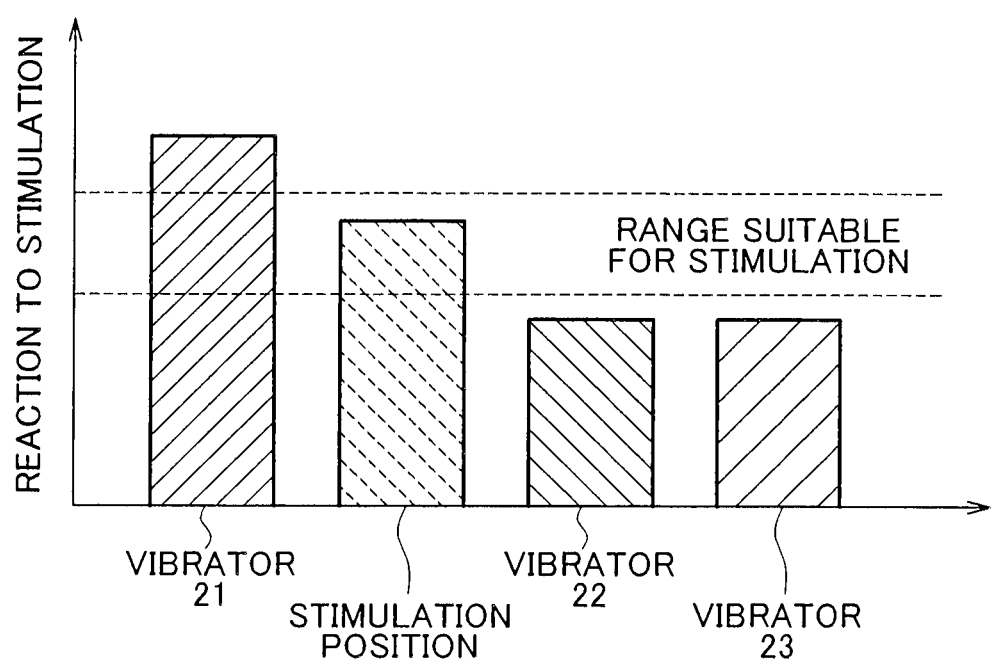
FIG. 30 is a graph illustrating how much the target person reacts to the stimulation to each of the positions of the respective vibrators and the stimulation position, shown in FIG. 2.

In the example embodiment, further, even if the vibrators 21 to 23 are not located at the stimulation positions due to the height of the target person M and/or his or her way of sitting, stimulation can be performed to each stimulation position. For example, referring to FIGS. 2 and 30, in a case where the perceptivity (or sensitivity) of the target person M to the stimulation is different between the respective stimulation positions and an intermediate stimulation position Ps through which a stimulation reaction within a range suitable for stimulation can be obtained exists between the vibrators 21 to 23, the stimulation execution portion 15 of the sleep system 1 performs stimulation also on the intermediate stimulation position Ps between the vibrators 21 to 23. If the intermediate stimulation position Ps is equidistant from the vibrators 21 and 22, stimulation on the intermediate stimulation position Ps can be performed by stimulating the two positions via the vibrators 21 and 22 simultaneously at the same stimulation level.

Figure 31:
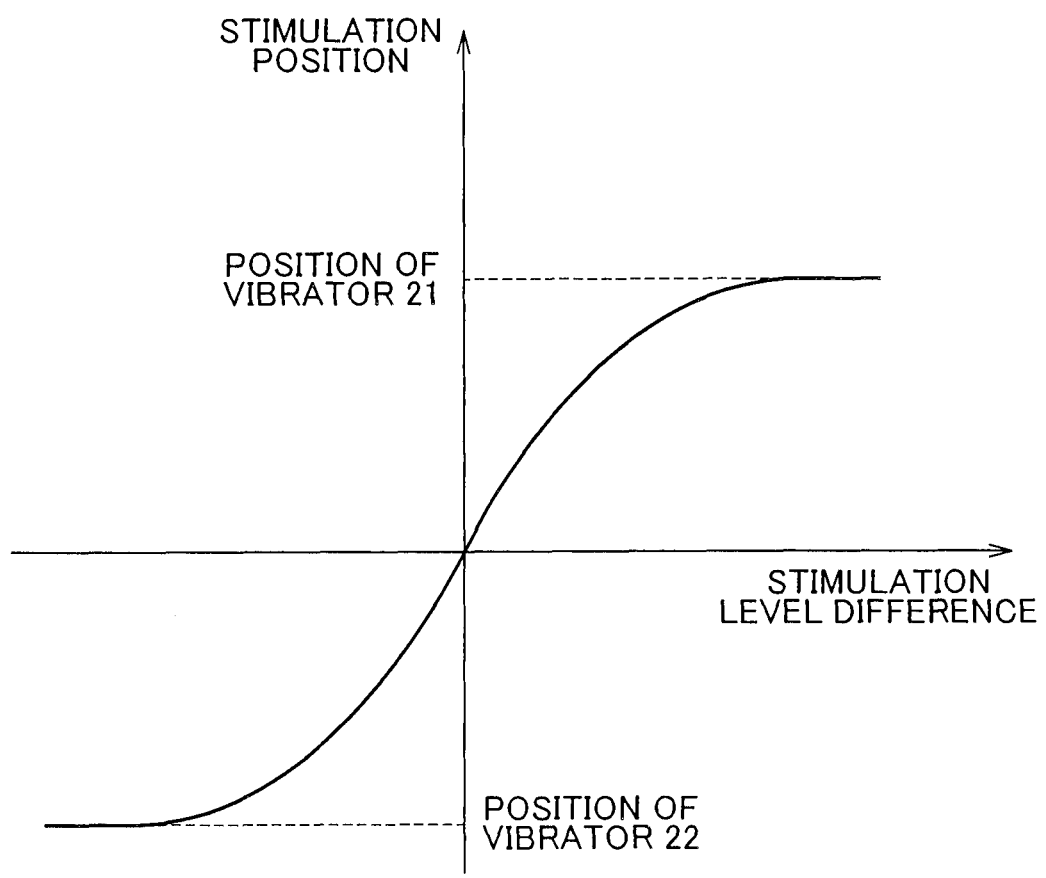
FIG. 31 is a graph illustrating a non-linear relation between the stimulation position and the difference between the stimulation levels of the respective vibrators, shown in FIG. 2.
Figure 32:
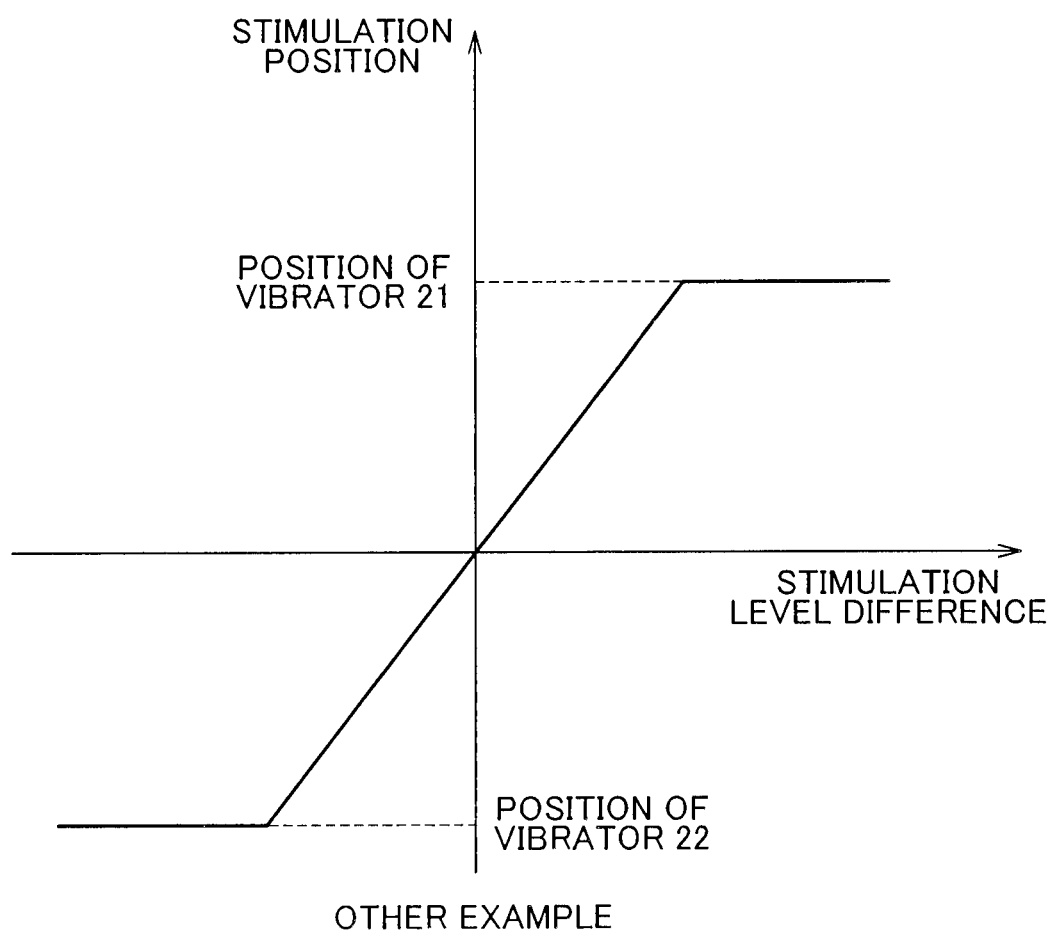
FIG. 32 is a graph illustrating a linear relation between the stimulation position and the difference between the stimulation levels of the respective vibrators, shown in FIG. 2.

On the other hand, if the intermediate stimulation position Ps is not equidistant from the vibrators 21 and 22, the stimulation execution portion 15 performs the stimulation on the intermediate stimulation position Ps by activating the vibrators 21 and 22 simultaneously at different stimulation levels. Referring to FIG. 31, the stimulation manner determination portion 14 may determine the stimulation levels of the vibrators 21 and 22 using, the relation between the stimulation position and the difference between the stimulation levels of the vibrators 21 and 22, which is stored in the stimulation timing database 17. In such a case, the stimulation manner determination portion 14 may alternatively use a linear relation, such as the one illustrated in FIG. 32. Further, the stimulation level may be increased without changing the stimulation position. Further, the positions of the vibrators 21 to 23 may be mechanically moved. These methods are known as methods utilizing a phantom sensation that when a person is stimulated at two positions at the same level, he or she feels stimulated at a position between the two positions at substantially the same level.

Figure 33:
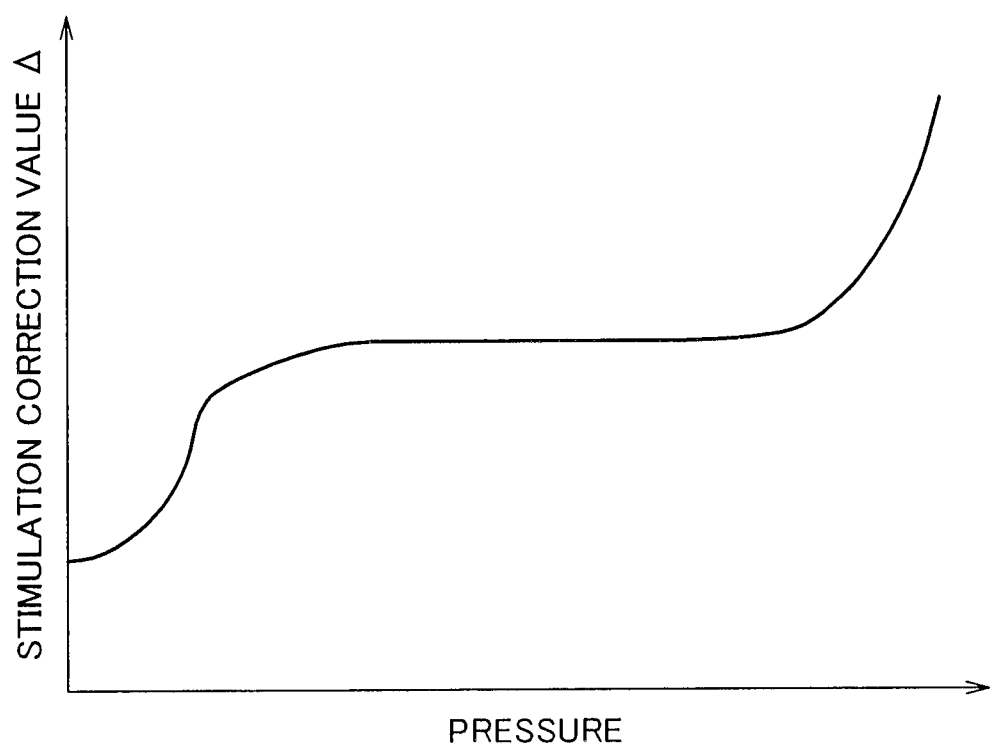
FIG. 33 is a graph illustrating a relation between the pressure on the seat and the stimulation correction value.
Figure 34:
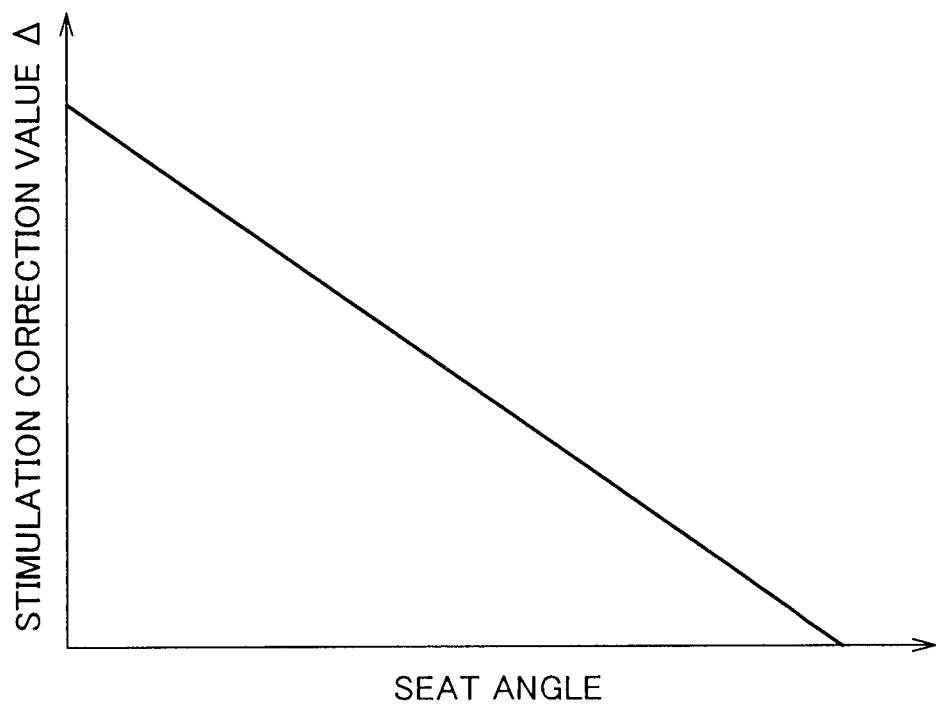
FIG. 34 is a graph illustrating a relation between the seat angle and the stimulation correction value.

In the example embodiment, further, the stimulation level may be changed factoring in the influence of the pressure on the seat 20. Referring to FIG. 26, the stimulation manner determination portion 14 detects the pressure on the seat 20 and the seat angle using the pressure-acceleration sensors 28 and the seat angle sensor 26 (S405). Referring to FIGS. 33 and 34, a stimulation correction value Δ for the seat pressure or a stimulation, correction value Δ for the seat angle is stored in the stimulation timing database 17. The stimulation manner determination portion 14 corrects the stimulation level by referring to the stimulation correction value Δ for the seat pressure or to the stimulation correction value Δ for the seat angle, which is stored in the stimulation timing database 17 (S406). At this time, the stimulation manner determination portion 14 may calculate the stimulation level by multiplying the value of the seat pressure or the value of the seat angle by a given coefficient (S406).

The stimulation manner determination portion 14 may determine the build of the target person M by calculating it from the pressure applied during movement of his or her body, the amplitude of the values detected by the pressure-acceleration sensors 28, and the rate of change in the same value, or from their integral values. In a case where the pressure-acceleration sensors 28 are not provided in the seat 20, the stimulation manner determination portion 14 may calculate the pressure on the seat 20 from voltage and current variations during that occurs when the vibrators 21 to 23 are pressured. The stimulation manner determination portion 14 further corrects, if necessary, the stimulation level while observing the stimulation effect. Meanwhile, it is considered that the larger the load on the seat 20, the more largely the sensory organs of the target person M deform, and thus the more likely his or her perceptivity or sensitivity is to decrease. However, in a case where the target person M is of an average build, it is believed that his or her perceptivity or sensitivity does not change significantly even if he or she changes the angle of the seatback of the seat 20.

Figure 35:
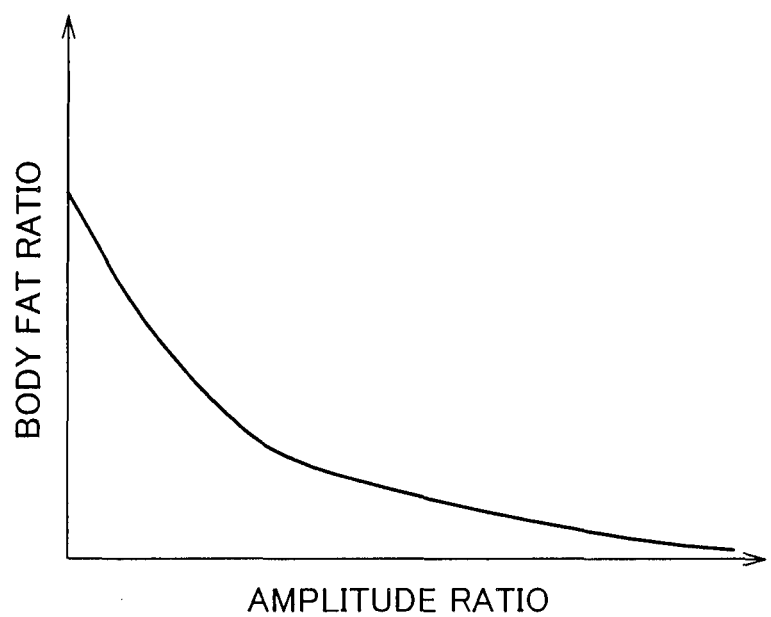
FIG. 35 is a graph illustrating a relation between the body fat ratio of the target person and the ratio of the amplitude detected by the pressure-acceleration sensor to the amplitude of the vibrators.

In the example embodiment, further, the stimulation level is corrected based on the vibration propagation differences due to the build of each target person M. Further, the influence of the clothes of the target person M may be factored in. Referring to FIGS. 3 and 26, the stimulation manner determination portion 14 vibrates the target person M using the vibrators 21 to 23 and measures the vibration amplitude using the pressure-acceleration sensors 28. The stimulation manner determination portion 14 calculates the ratio between the amplitude of the vibration applied using the vibrators 21 to 23 and the amplitude measured by the pressure-acceleration sensors 28 (decay rate). Referring to FIG. 35, a relation between the amplitude ratio described above and the body fat ratio of the target person M is stored in the stimulation timing database 17. The stimulation manner determination portion 14 calculates the body fat ratio of the target person M by referring to the relation between the amplitude ratio and the body fat ratio of the target person M, which is stored in the stimulation timing database 17 (S407).

Figure 36:
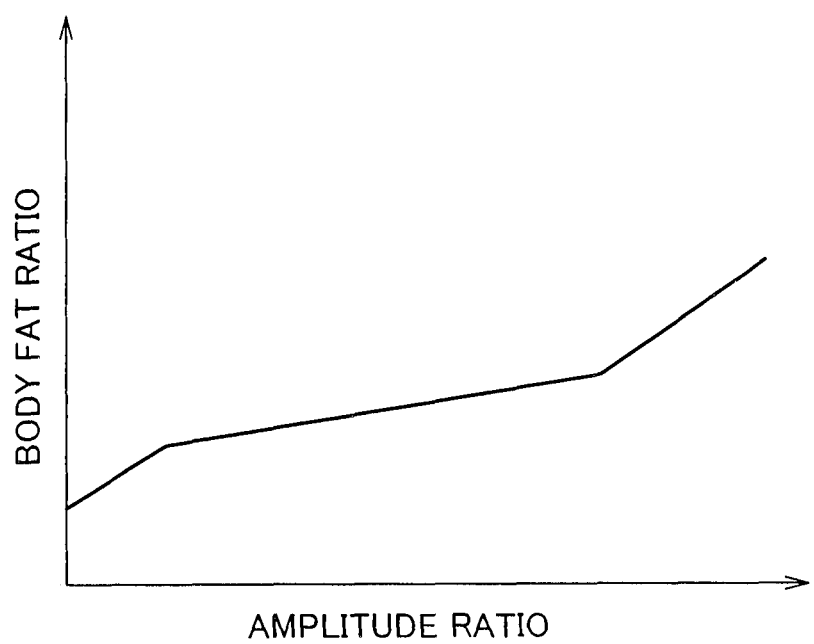
FIG. 36 is a graph illustrating a relation between the body fat ratio of the target person and the biological reaction amount.

Further, referring to FIG. 36, a relation between the body fat ratio of the target person M and the stimulation level is stored in the stimulation timing database 17. The stimulation manner determination portion 14 changes the stimulation level by referring to the relation between the body fat ratio of the target person M and the stimulation level, which is stored in the stimulation timing database 17 (S408). Meanwhile, the stimulation manner determination portion 14 may determine the degree of vibration propagation through a comparison between the frequencies at the positions of the respective pressure-acceleration sensors 28 and the frequencies at the positions of the respective vibrators 21 to 23. Further, the stimulation manner determination portion 14 may calculate the stimulation level according to the logarithms of the amplitudes and/or those of the frequencies.

Figure 37:
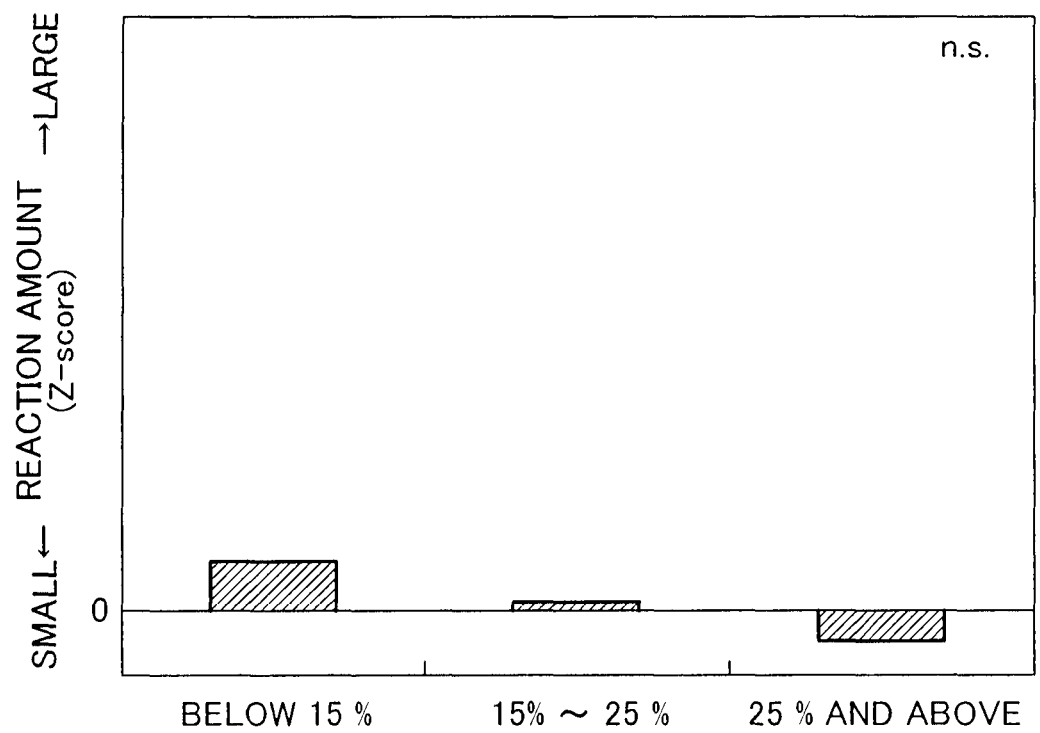
FIG. 37 is a graph illustrating a relation between the body fat ratio of the target person and the electrodermal activity of the target person.
Figure 38:
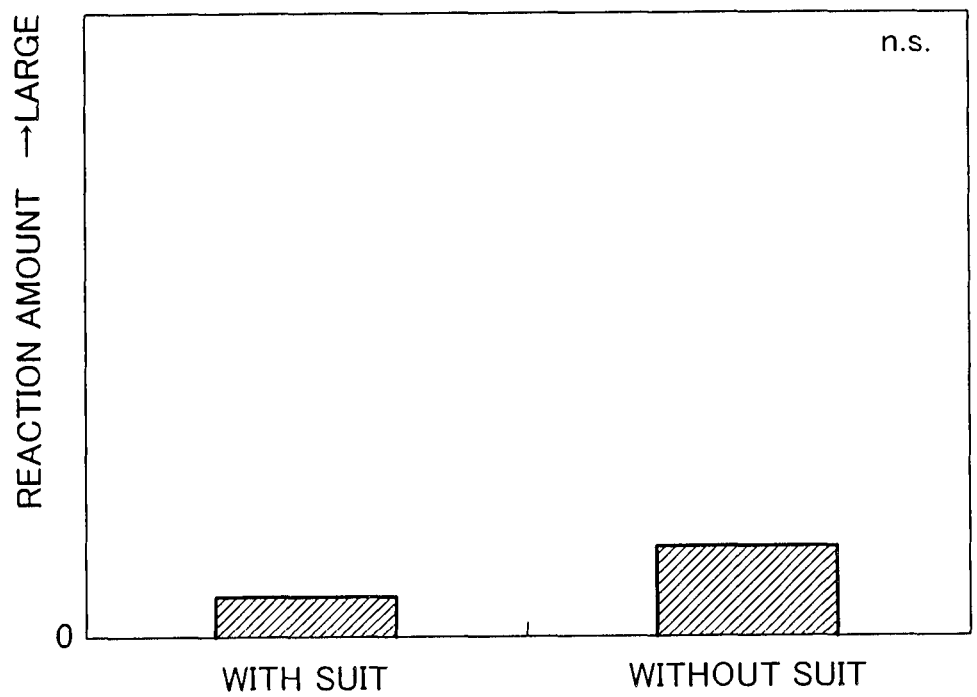
FIG. 38 is a graph illustrating a relation between the biological reaction amount in a case where the target person is wearing a suit and the biological reaction amount in a case where the target person is not wearing a suit.

FIG. 37 illustrates, by way of example, a relation between the body fat ratio and the sensitivity. As is known from FIG. 37, the higher the body fat ratio, the lower the sensitivity. Thus, if the body fat ratio of the target person M is low and therefore he or she senses even a weak stimulus, the stimulation manner determination portion 14 lowers the stimulation level. However, it is to be noted that a slight difference in body fat ratio does not cause a significant change in the sensitivity as shown in FIG. 37. Further, referring to FIG. 38, the sensitivity of the target person M varies depending upon whether he or she is wearing a suit. Therefore; the stimulation manner determination portion 14 may also factor in such a sensitivity difference due to the clothes of the target person M, using the method described above. If the stimulation level does not reach the target stimulation level, the stimulation manner determination portion 14 further increases the stimulation level.

Figure 39:
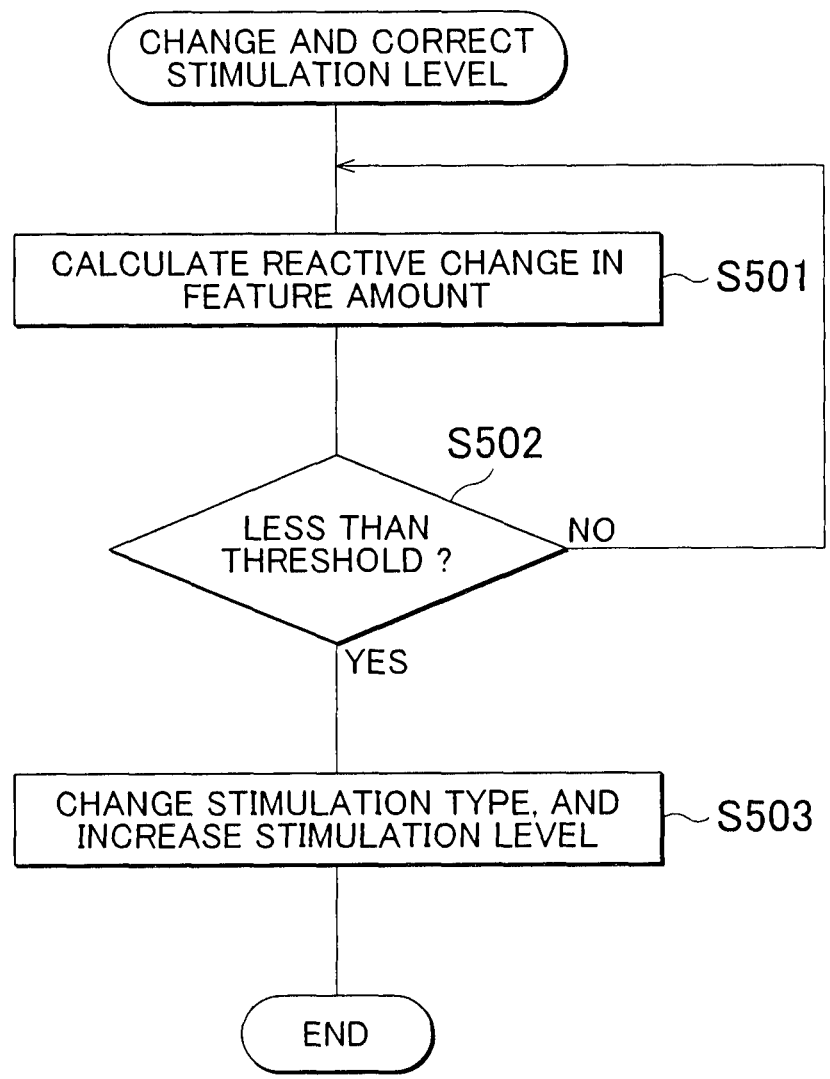
FIG. 39 is a flowchart illustrating an operation procedure for changing and correction the stimulation level in the operation procedure illustrated in FIG. 4.

In the example embodiment, further, the stimulation level and method are changed in the light of the adaptability of the target person M to stimulation. Referring to FIG. 39, the stimulation manner determination portion 14 calculates the amount by which a given feature amount changes in reaction to the stimulation (S501). This reaction amount may be the reaction rate per unit time, the ratio of the present reaction amount to the last reaction amount, or the ratio of the present reaction amount to the average reaction amount. The stimulation manner determination portion 14 changes the type of stimulation or increases the stimulation level (S503) in response to the reaction amount becoming smaller than a threshold (S502).

For example, the stimulation manner determination portion 14 changes the stimulation level when the amount of reaction to the stimulation has decreased or when the time interval at which to repeat the stimulation has been reduced. Further, the stimulation manner determination portion 14 increases the stimulation level when no reaction amount is detected in response to the stimulation or when the time interval at which to repeat the stimulation has been reduced by half. The stimulation manner determination portion 14 measures the degree of adaptability of the target person M to the stimulation, from the reaction ratio obtained after the stimulation, and then changes the stimulation level and the stimulation type. This reaction ratio may be, for example, the ratio between the number of times a reaction occurs in a given period of time and the number of times the stimulation is performed in the same period of time, or the ratio between the average reaction amount over a given period of time and the average reaction amount over the same period of time in the last measurement cycle (duration).

Figure 40:
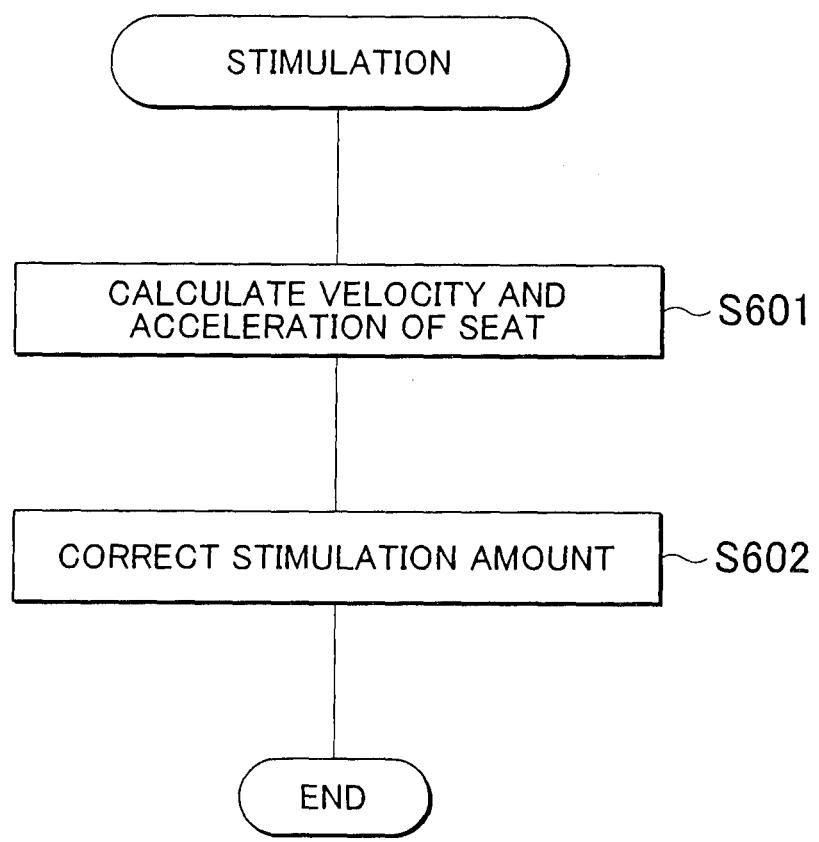
FIG. 40 is a flowchart illustrating detailed operation for the stimulation in the operation procedure illustrated in FIG. 4.
Figure 41:
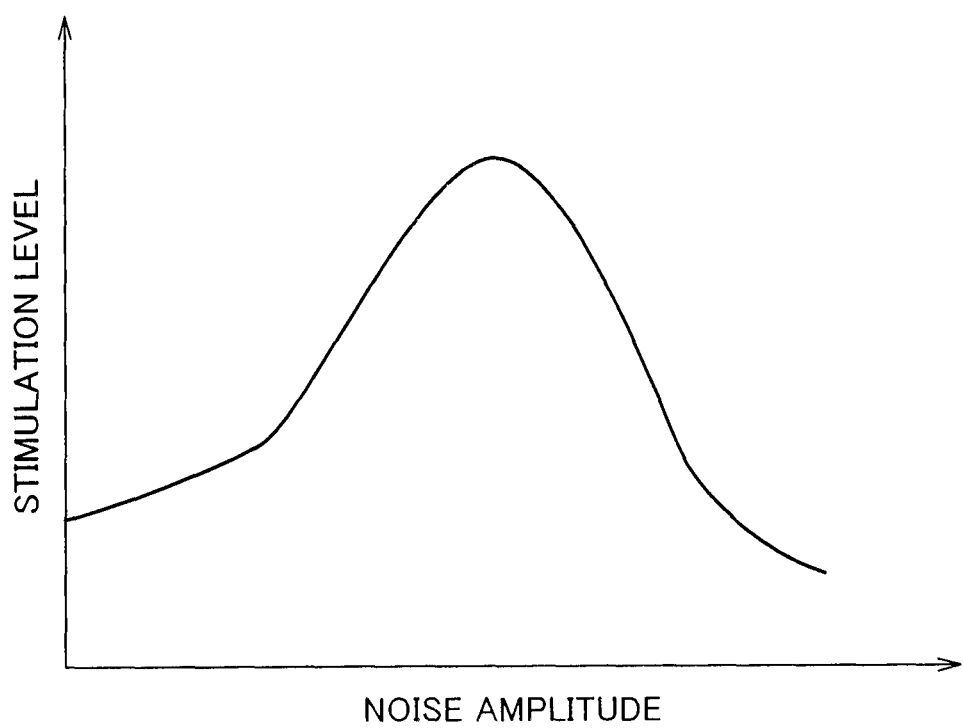
FIG. 41 is a graph illustrating a relation between the amplitude of a noise propagating to the seat or bed and the stimulation level.

In the example embodiment, further, the stimulation level may be increased using the vibrations and noises in the vehicle. Referring to FIG. 40, the stimulation manner determination portion 14 calculates the velocity and acceleration of the seat 20 from the values detected by the pressure-acceleration sensors 28 (S601). Referring to FIG. 41, a relation between the noise amplitude and the stimulation level is stored in the stimulation timing database 17. Referring to this relation stored in the stimulation timing database 17, the stimulation manner determination portion 14 corrects the stimulation amount by calculating the stimulation level based on the noise amplitude (S602).

With regard to such vibrations, if the application is a vehicle, the stimulation manner determination portion 14 presets an amplitude(s) that develops a high stimulation effect, based on the material of the seat 20, the vehicle speed, the characteristics of the suspension systems, and so on. In a case where the vehicle is provided with an active suspension system, the stimulation manner determination portion 14 changes its damping rate in accordance with the vehicle speed, and sets an amplitude for developing a high stimulation effect. The stimulation manner determination portion 14 performs this setting such that the vibration and noise frequencies become those of white noises or those of pink noises.

According to the example embodiment, applying the stimulus determined based on the difference between the present sleep depth of the target person M, which is detected by the stimulation effect calculation portion 13, and the target sleep depth for the target person M, the stimulation execution portion 15 of the sleep system 1 is capable of applying, in accordance with the present sleep depth of the target person M, a stimulus more appropriate than that applied simply according to the target sleep depth. As such, the sleep depth of the target person M can be easily maintained at the target sleep depth.

According to the example embodiment, further, since the stimulation execution portion 15 applies a stimulus of a higher level, the larger the difference between the present sleep depth of the target person M and the target sleep depth for the target person M, and therefore the stimulation execution portion 15 is capable of applying a stimulus of an appropriate level in accordance with the same difference.

According to the example embodiment, further, the stimulation execution portion 15 applies a stimulus of a higher level, the larger the present sleep depth of the target person M, and therefore the stimulation execution portion 15 is capable of applying a stimulus of an appropriate level in accordance with the present sleep depth of the target person M.

According to the example embodiment, further, in a case where the stimulation effect calculation portion 13 is unable to measure the present sleep depth of the target person M after the target person M has been stimulated, the stimulation execution portion 15 stimulates the target person M again upon lapse of a predetermined period of time, independently of the difference between the present sleep depth of the target person M and the target sleep depth for the target person M, and therefore the stimulation execution portion 15 is capable of reliably stimulating the target person M even when the present sleep depth of the target person M has been immeasurable. As such, for example, it is possible to cope with even a case where the physiological waveform becomes unsteady due to an external disturbance from the stimulation and thus the sleep depth of the target person M becomes immeasurable.

According to the example embodiment, further, the stimulation effect calculation portion 13 measures the present sleep depth of the target person M based on the brainwaves of the target person M that develop immediately after the stimulation execution portion 15 stimulates the target person M. As such, for example, even in a case where the physiological waveform becomes unsteady due to an external disturbance from the stimulation, it is possible to accurately measure the present sleep depth of the target person M by examining the effect of the stimulation.

According to the example embodiment, further, when the amount by which the present sleep depth changes in response to the stimulation has decreased, or when the frequency at which to apply the stimulus determined based on the difference between the sleep depth of the target person M and the target sleep depth for the target person M has decreased, it is considered that the target person M has been adapted to the stimulation and thus the stimulation effect has decreased. In such a case, therefore, the stimulation execution portion 15 applies a stimulus of a higher level. As such, it is easy to constantly stimulate the target person M at an appropriate level.

According to the example embodiment, further, the stimulation execution portion 15 stimulates the target person M using either vibrations or noises around the target person M, and thus even a small element can provide a high stimulation effect on the target person M using, for example, vibrations and noises In the vehicle.

According to the example embodiment, further, the sleep system 1 is further provided with the stimulation effect calculation portion 13 that measures the amount of a biological reaction that occurs in response to the stimulus applied from the stimulation execution portion 15 before the target person falls asleep, and the stimulation manner determination portion 14 corrects the stimulus to be applied when the target person M is asleep, based on the biological reaction amount that the stimulation effect calculation portion 13 has measured before the target person M fell asleep. As such, it is easy to apply an appropriate stimulus to each target person M, regardless of his or her individuality and condition. Note that the structure of the example embodiment may be incorporated into various vehicles other than automobiles, such as airplanes and trains.

According to the example embodiment, further, the stimulation execution portion 15 is capable of stimulating the target person M at multiple positions, and the stimulation effect calculation portion 13 corrects the positions of the target person M to which the stimulation is performed when the target person M is asleep, based on the amount of the biological reaction to the stimulus applied to each of the positions before the target person M fell asleep, which was measured by the stimulation effect calculation portion 13. Thus, it is easy to stimulate appropriate positions of the target person M, regardless of how each target person M is seated on the seat and how each target person M lies in a bed. Further, the stimulation execution portion 15 corrects the position(s) of the target person M to which the stimulation is performed when the target person M is asleep, by changing the stimuli applied, respectively, to multiple positions of the target person M. As such, even in a case where an intermediate position between the positions to which stimuli can be applied is the position suitable for stimulation, the intimidate position can be properly stimulated by changing the stimuli applied, respectively, to the former positions. Note that the stimulation effect calculation portion 13 serves also as "biological reaction measurement portion".

According to the example embodiment, further, the stimulation manner determination portion 14 corrects the stimulus to be applied to the target person M, based on at least one of the pressure oh the seat 20 on which the target person M is seated and the tilt angle of the seat 20, or based on at least one of the pressure on the bed in which the target person M lies and the tilt angle of the bed. As such, it is easy to stimulate the target person M properly, regardless of how the target person M is seated or lies and what build the target person M has.

According to the example embodiment, further, the stimulation manner determination portion 14 corrects the stimulus to be applied to the target person M, based on the vibration propagation to the body of the target person M. As such, it is easy to stimulate the target person M properly, regardless of what build, shape, and body fat ratio the target person M has.

The invention has been described with reference to the example embodiment for illustrative purposes only. It should be understood that the description is not intended to be exhaustive or to limit form of the invention and that the invention may be adapted for use in other systems and applications. The scope of the invention embraces various modifications and equivalent arrangements that may be conceived by one skilled in the art.

The invention claimed is:

1. A sleep system, comprising:
a sleep depth measurement unit that measures a present sleep depth of a target person; and
a stimulation execution unit that stimulates the target person, wherein
the stimulation execution unit applies a stimulus that is determined based on a difference between the present sleep depth of the target person, which is measured by the sleep depth measurement unit, and a target sleep depth for the target person, which is used as a target, and the larger the present sleep depth of the target person is, the higher level of stimulus the stimulation execution unit applies, with respect to the same difference.

2. A sleep system according to claim 1, wherein
the stimulation execution unit stimulates again the target person, regardless of the difference between the present sleep depth of the target person and the target sleep depth for the target person, upon lapse of a predetermined period of time in a case where the sleep depth measurement unit is unable to measure the present sleep depth of the target person after the stimulation execution unit stimulates the target person.

3. A sleep system according to claim 1, wherein
the sleep depth measurement unit measures the present sleep depth of the target person based on a content ratio of at least one of beta waves, alpha waves, theta waves, delta waves, and sigma waves of brainwaves of the target person that develop immediately after the stimulation execution unit stimulates the target person, and a shift of a sleep stage of the target person, and
the stimulation execution unit applies a stimulus that is determined based on a difference between the present sleep depth of the target person, which is measured by the sleep depth measurement unit, and a target sleep depth for the target person, which is used as a target.

4. A sleep system according to claim 1, wherein
a sleep depth measurement unit that measures a present sleep depth of a target person; and
the stimulation execution unit applies a stimulus of a higher level in one of a case where an amount by which the present sleep depth of the target person changes in response to a stimulus applied by the stimulation execution unit has decreased and a case where a frequency at which to apply a stimulus determined based on the difference between the present sleep depth of the target person and the target sleep depth for the target person has decreased.

5. A sleep system according to claim 1, wherein
the stimulation execution unit corrects a stimulus to be applied to the target person based on a level of stimulus that is applied to the target person by either vibrations or noises around the target person.

6. A sleep system according to claim 1 further comprising:
a biological reaction amount measurement unit that measures one of heartbeat, blood pressure, respiration, electrodermal activity, body temperature, and eye movement in response to a stimulus applied by the stimulation execution unit before the target person falls asleep, wherein
the stimulation execution unit corrects a stimulus that is applied to the target person when the target person is asleep, based on one of the heartbeat, the blood pressure, the respiration, the electrodermal activity, the body temperature, and the eye movement before falling asleep, which is measured by the biological reaction amount measurement unit.

7. A sleep system according to claim 1 further comprising:
a biological reaction amount measurement unit that measures an amount of a biological reaction to a stimulus applied by the stimulation execution unit before the target person falls asleep, wherein
the stimulation execution unit is capable of stimulating multiple positions of the target person, and
the stimulation execution unit corrects positions to be stimulated when the target person is asleep, by changing stimuli applied simultaneously to the multiple positions, based on the amount of a biological reaction to a stimulus applied to each of the multiple positions before falling asleep, which is measured by the biological reaction amount measurement unit.

8. A sleep system according to claim 1, wherein
the stimulation execution unit corrects a stimulus to be applied to the target person, based on one of a pressure on a seat on which the target person is seated or on a bed in which the target person lies, and a tilt angle of the seat on which the target person is seated or of the bed in which the target person lies.

9. A sleep system according to claim 1, wherein
the stimulation execution unit stimulates the target person using a vibration, and corrects a stimulus to be applied to the target person based on propagation of the vibration to a body of the target person.

10. The sleep system according to claim 1, wherein the larger the difference between the present sleep depth of the target person and the target sleep depth for the target person is, the higher level of stimulus the stimulation execution unit applies.

* * * * *